United States Patent
Yang et al.

(10) Patent No.: US 11,161,789 B2
(45) Date of Patent: Nov. 2, 2021

(54) HIGHLY TRANSLUCENT ZIRCONIA MATERIAL, DEVICE, METHODS OF MAKING THE SAME, AND USE THEREOF

(71) Applicant: James R. Glidewell Dental Ceramics, Inc., Newport Beach, CA (US)

(72) Inventors: Yan Yang, Irvine, CA (US); Sreeram Balasubramanian, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 16/545,789

(22) Filed: Aug. 20, 2019

(65) Prior Publication Data

US 2020/0062653 A1 Feb. 27, 2020

Related U.S. Application Data

(60) Provisional application No. 62/721,340, filed on Aug. 22, 2018.

(51) Int. Cl.
*C04B 35/48* (2006.01)
*A61K 6/818* (2020.01)
*A61K 6/824* (2020.01)

(52) U.S. Cl.
CPC .............. *C04B 35/48* (2013.01); *A61K 6/818* (2020.01); *A61K 6/824* (2020.01); *C04B 2235/3225* (2013.01); *C04B 2235/3246* (2013.01); *C04B 2235/5436* (2013.01); *C04B 2235/5463* (2013.01); *C04B 2235/77* (2013.01); *C04B 2235/9646* (2013.01)

(58) Field of Classification Search
CPC ...... C04B 35/486; C04B 35/488; A61K 6/818
See application file for complete search history.

(56) References Cited

U.S. PATENT DOCUMENTS

| | | | |
|---|---|---|---|
| 4,279,655 A | 7/1981 | Garvie et al. | |
| 5,326,518 A | 7/1994 | Kimura et al. | |
| 6,087,285 A | 7/2000 | Oomichi et al. | |
| 7,806,694 B2 | 10/2010 | Brodkin et al. | |
| 8,815,760 B2 * | 8/2014 | Watanabe | C04B 35/486 501/103 |
| 8,936,848 B2 | 1/2015 | Jung et al. | |
| 9,095,403 B2 | 8/2015 | Carden et al. | |
| 9,309,157 B2 | 4/2016 | Fujisaki et al. | |
| 9,365,459 B2 | 6/2016 | Carden et al. | |
| 9,434,651 B2 | 9/2016 | Carden | |
| 9,505,662 B2 | 11/2016 | Carden et al. | |
| 9,512,317 B2 | 12/2016 | Carden et al. | |
| 9,737,383 B2 * | 8/2017 | Fujisaki | C04B 35/486 |
| 9,783,459 B2 | 10/2017 | Gottwik et al. | |
| 9,802,868 B2 | 10/2017 | Johannes et al. | |
| 10,004,668 B2 | 6/2018 | Brodkin et al. | |
| 2009/0115084 A1 | 5/2009 | Moon | |
| 2010/0003630 A1 | 1/2010 | Yamashita et al. | |
| 2011/0027742 A1 | 2/2011 | Fujisaki et al. | |

(Continued)

*Primary Examiner* — Karl E Group
(74) *Attorney, Agent, or Firm* — Charles Fowler

(57) ABSTRACT

A zirconia ceramic material for use in dental applications is provided comprising an yttria-stabilized zirconia material stabilized with 5 mol % yttria to 8 mol % yttria, and methods for making a sintered body from the ceramic material. The zirconia ceramic materials exhibit both enhanced translucency and a flexural strength of at least 300 MPa, or at least 500 MPa, when fully sintered.

20 Claims, 14 Drawing Sheets

SEM Of Sintered Yttria-Stabilized Zirconia Ceramic Body.

(56) References Cited

U.S. PATENT DOCUMENTS

| | | |
|---|---|---|
| 2012/0058883 A1 | 3/2012 | Yamashita et al. |
| 2012/0094823 A1* | 4/2012 | Watanabe ............ C04B 35/6455 |
| | | 501/134 |
| 2012/0277088 A1 | 11/2012 | Mathers et al. |
| 2013/0313738 A1 | 11/2013 | Carden |
| 2014/0227654 A1 | 8/2014 | Fujisaki et al. |
| 2016/0038381 A1 | 2/2016 | Jahns |
| 2016/0310245 A1* | 10/2016 | Fujisaki .................. A61C 7/14 |
| 2018/0002235 A1 | 1/2018 | Ito et al. |
| 2018/0235847 A1 | 8/2018 | Balasubramanian et al. |
| 2018/0237345 A1 | 8/2018 | Valenti et al. |
| 2021/0102115 A1* | 4/2021 | Kudo .................... C04B 35/634 |
| 2021/0102116 A1* | 4/2021 | Kudo .................... A61K 6/887 |

* cited by examiner

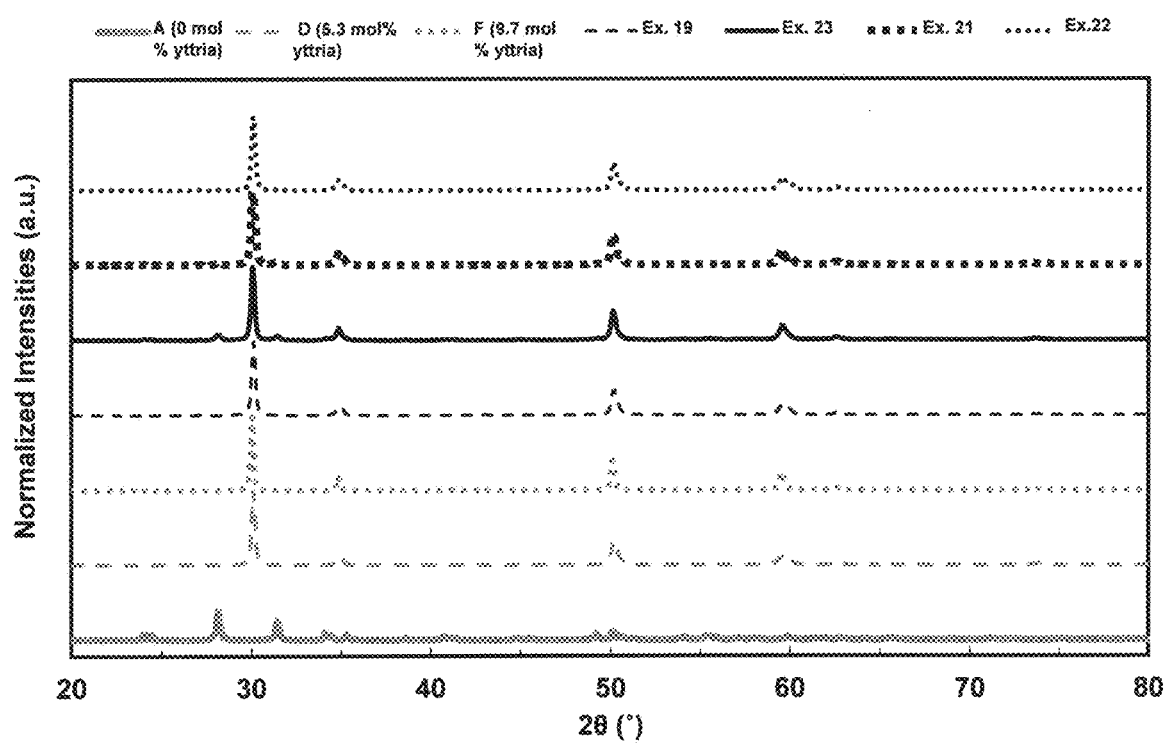
FIG. 5A. XRD of Bisque Yttria-Stabilized Zirconia Bodies With 5.9 mol% Yttria

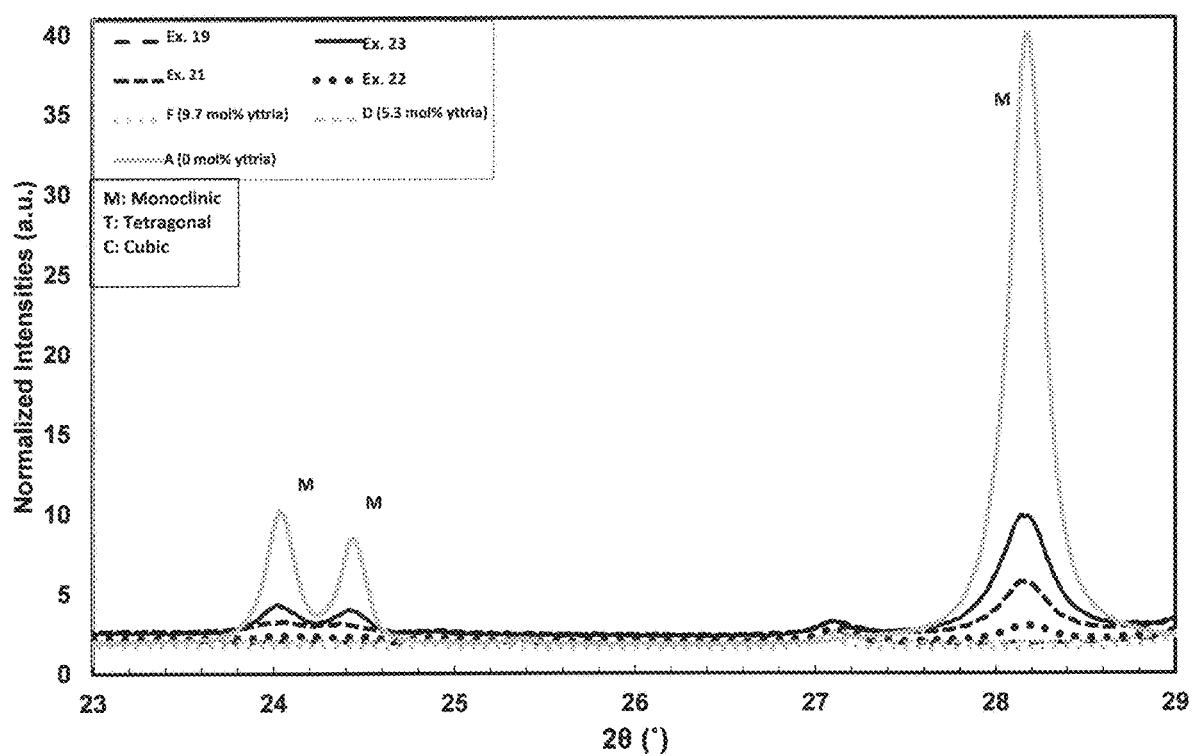

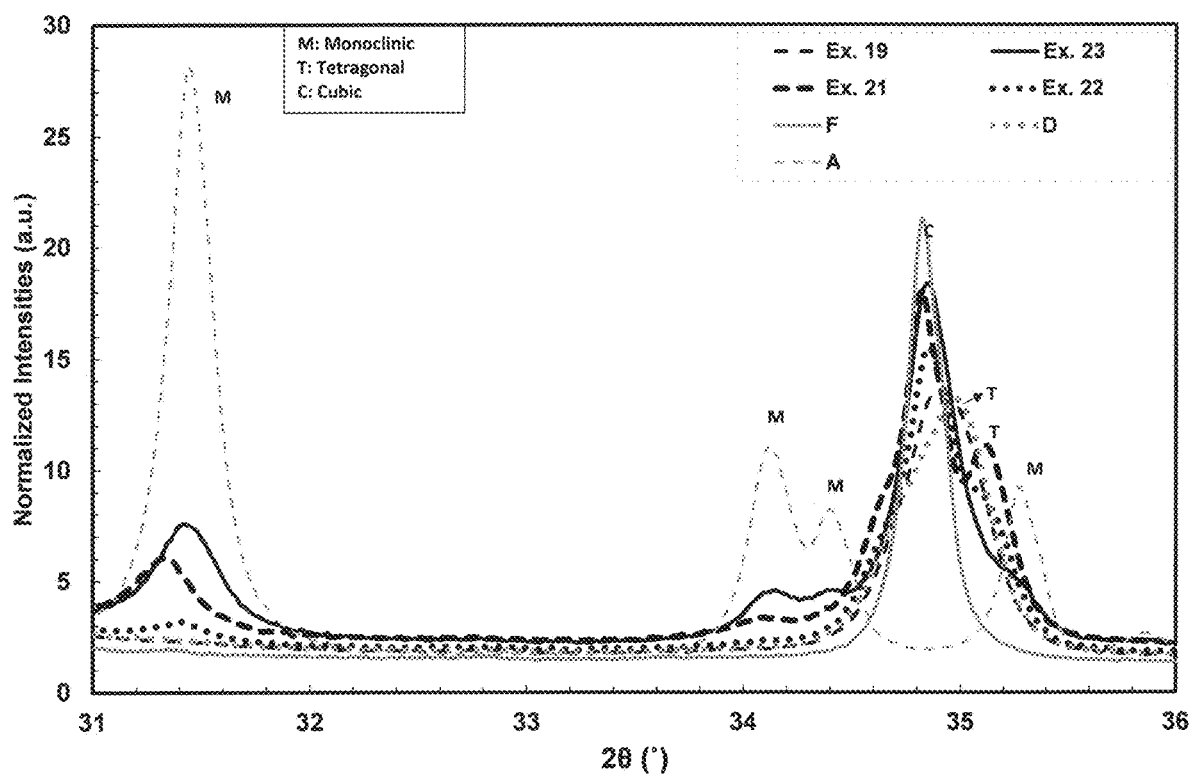
FIG. 5C. XRD Of Bisque Zirconia Bodies Having 5.9 mol% Yttria

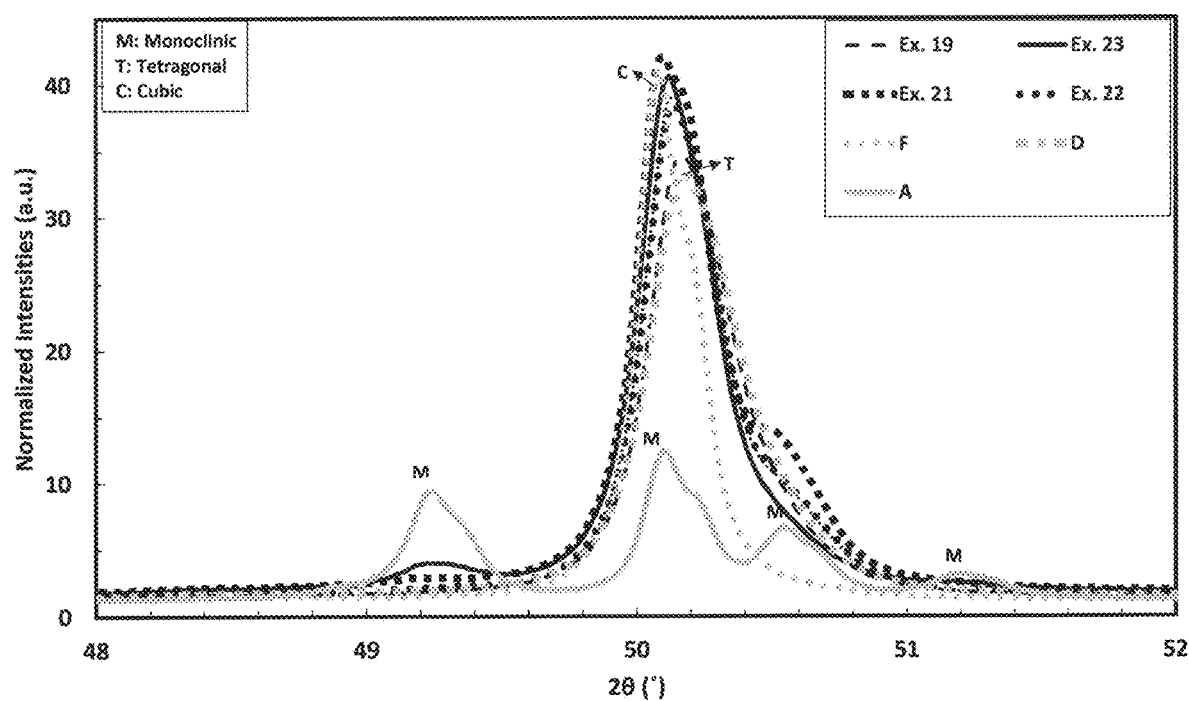
FIG. 5D. XRD Of Bisque Zirconia Bodies Having 5.9 Mol% Yttria

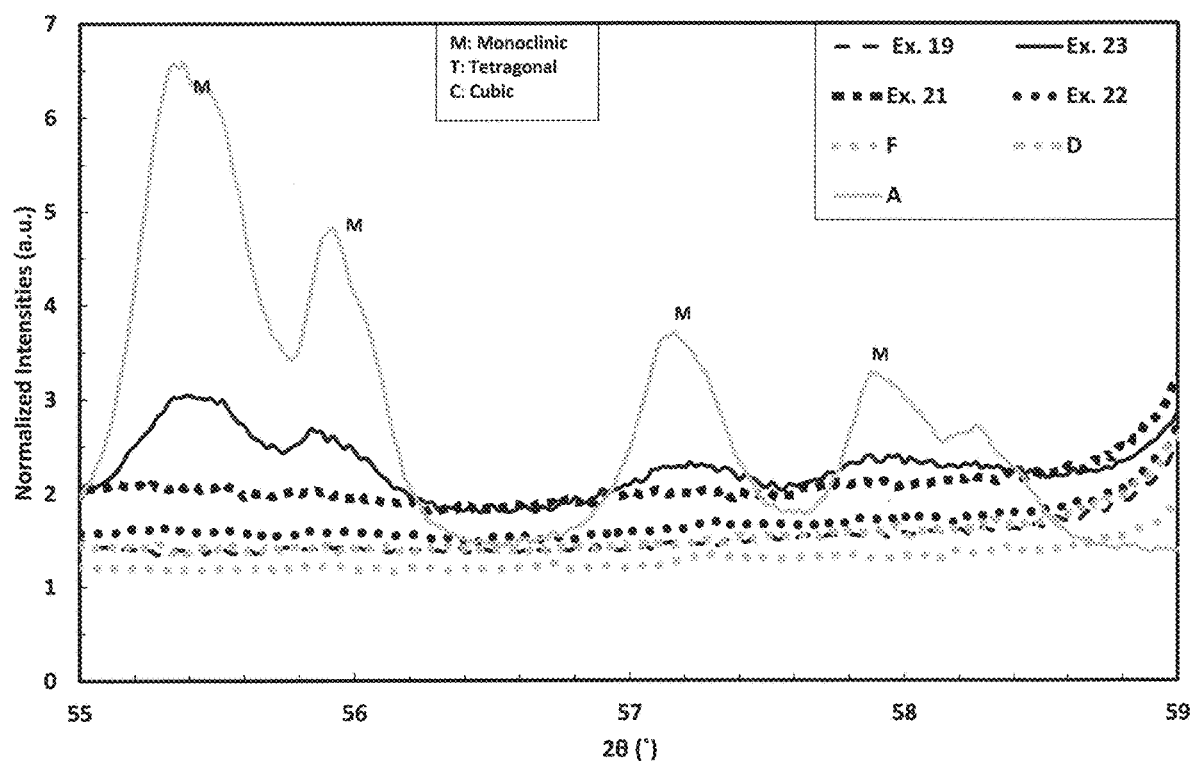

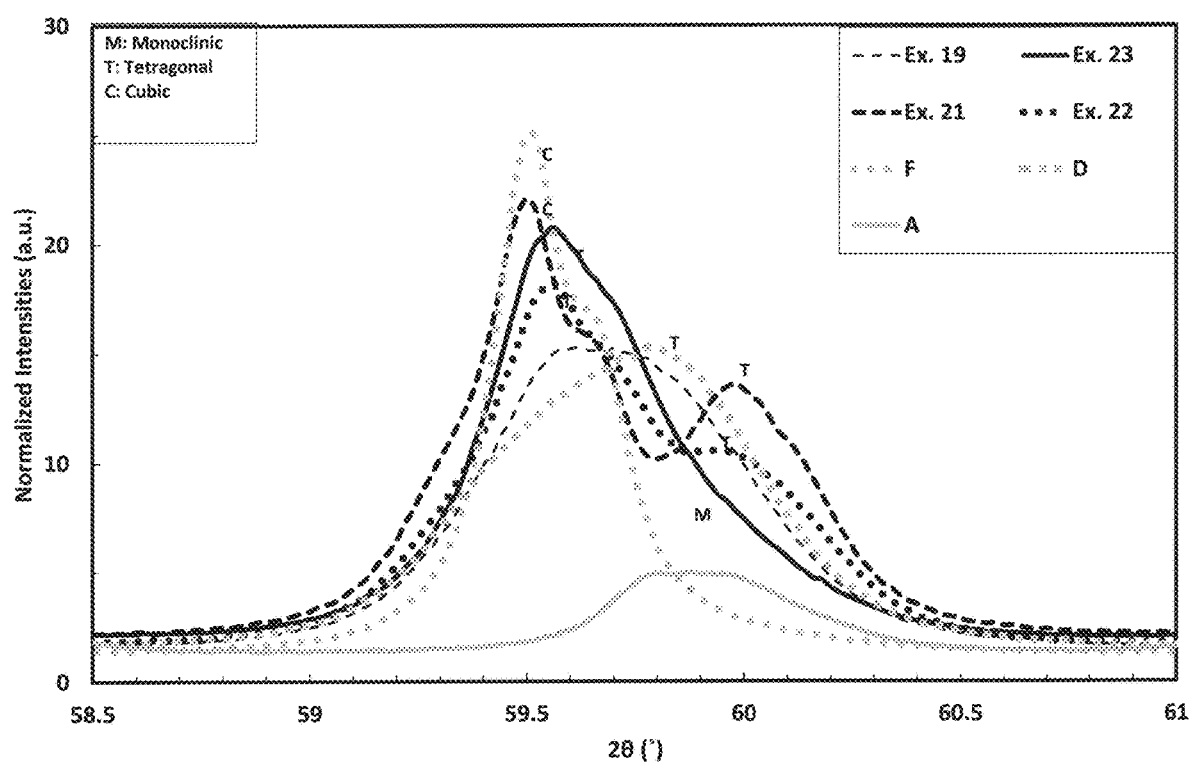
FIG. 5F. XRD of Bisque Zirconia Bodies Having 5.9 Mol% Yttria.

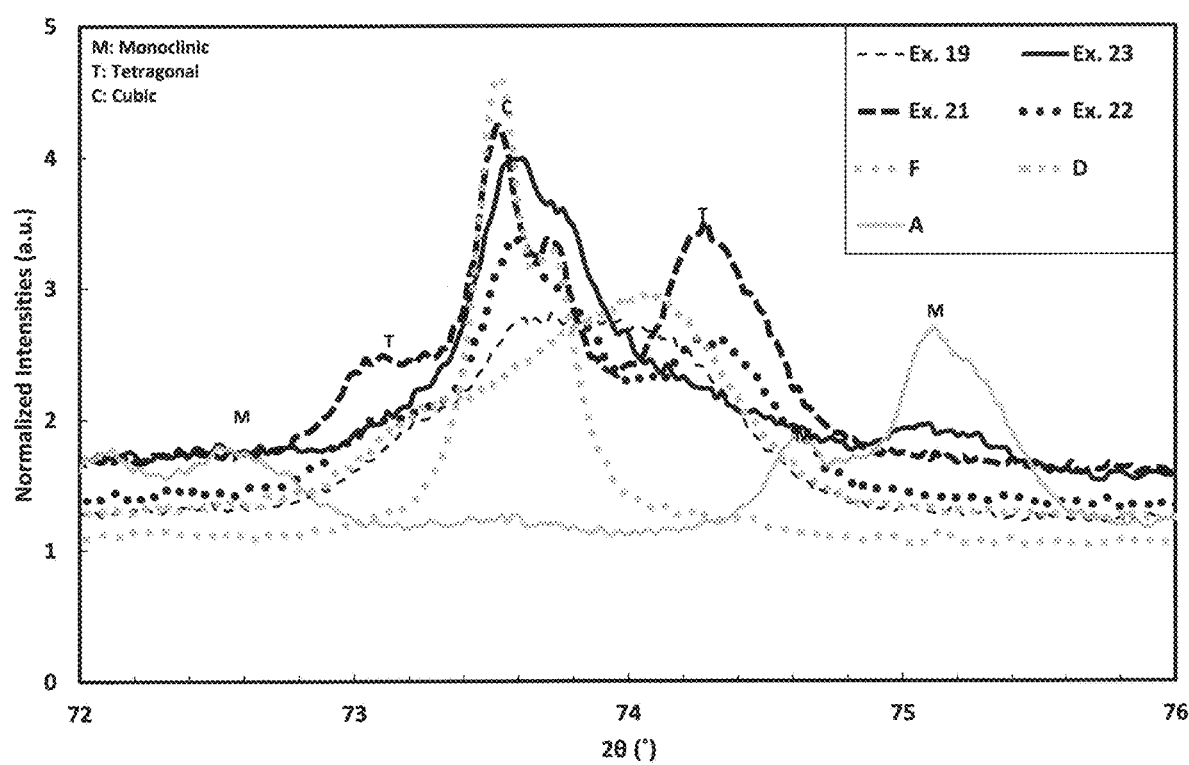
FIG. 5G. XRD Of Bisque Zirconia Bodies Having 5.9 Mol% Yttria.

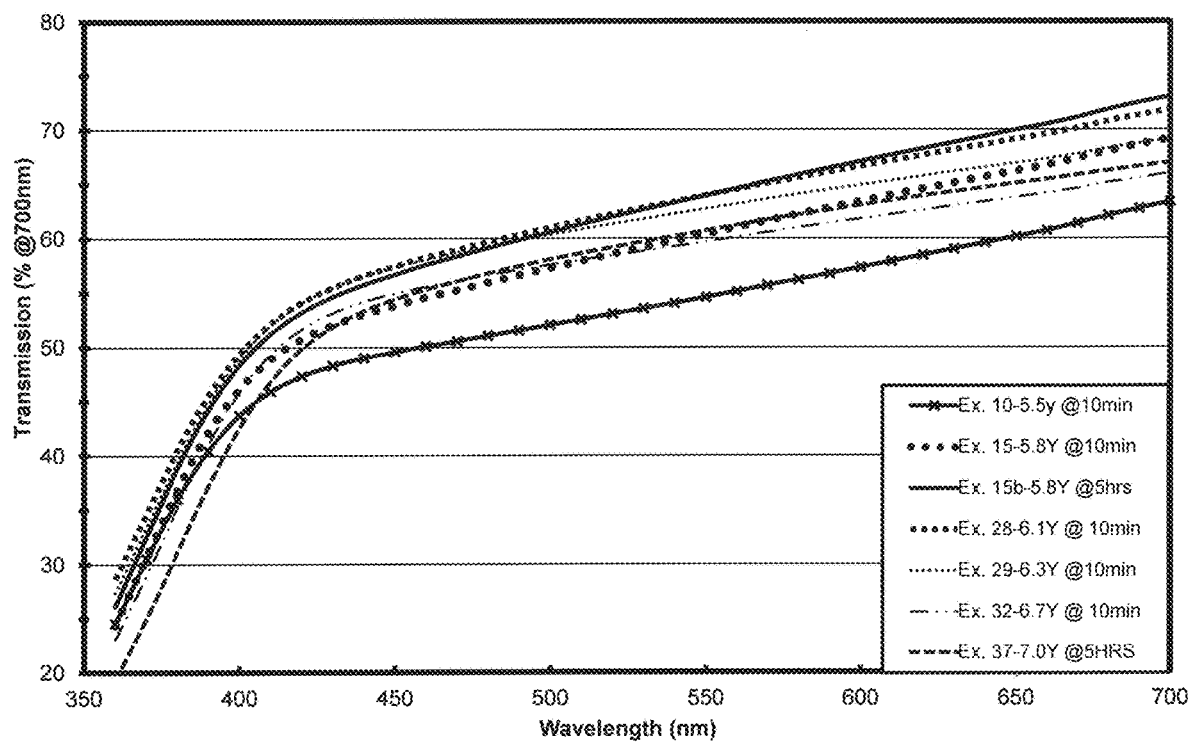

FIG. 7A. SEM Of Sintered Yttria-Stabilized Zirconia Ceramic Body.
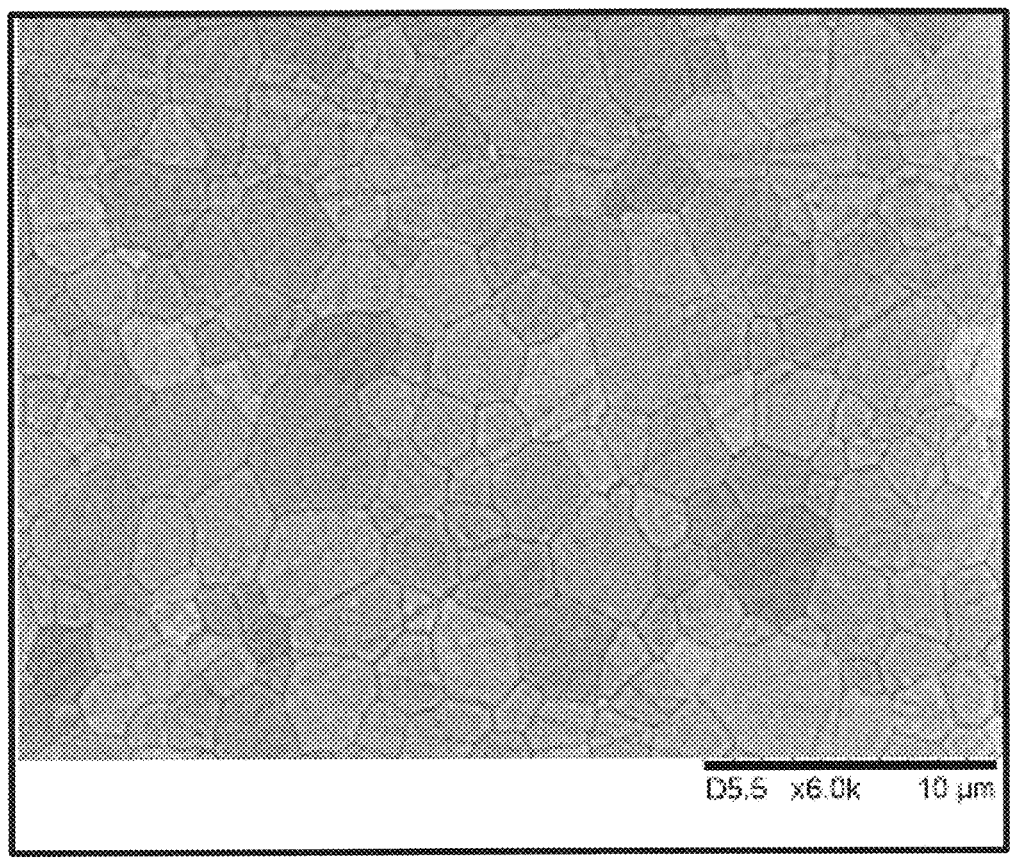

FIG. 7B. SEM Of Sintered Yttria-Stabilized Zirconia Ceramic Body
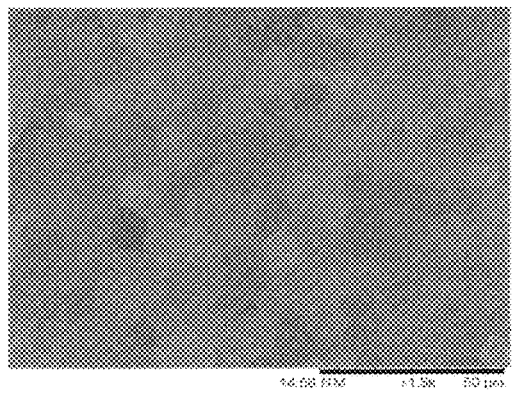
FIG. 7C. SEM Of Sintered Yttria-Stabilized Zirconia Ceramic Body
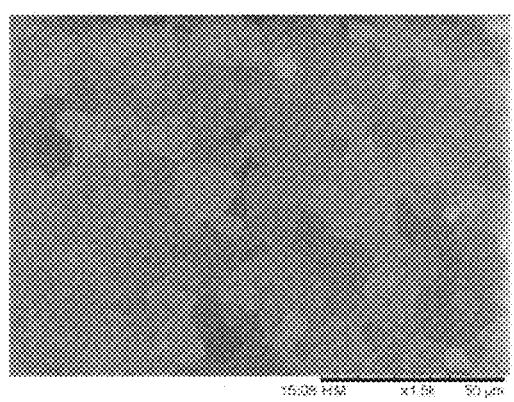
FIG. 7D. SEM Of Sintered Yttria-Stabilized Zirconia Ceramic Body
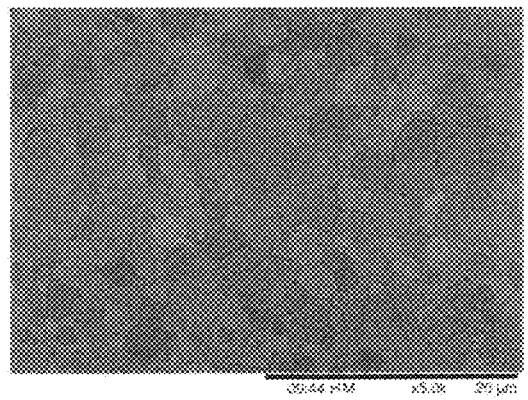
FIG. 7E. SEM Of Sintered Yttria-Stabilized Zirconia Ceramic Body
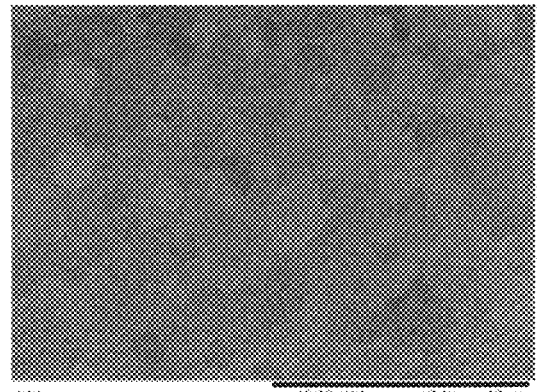

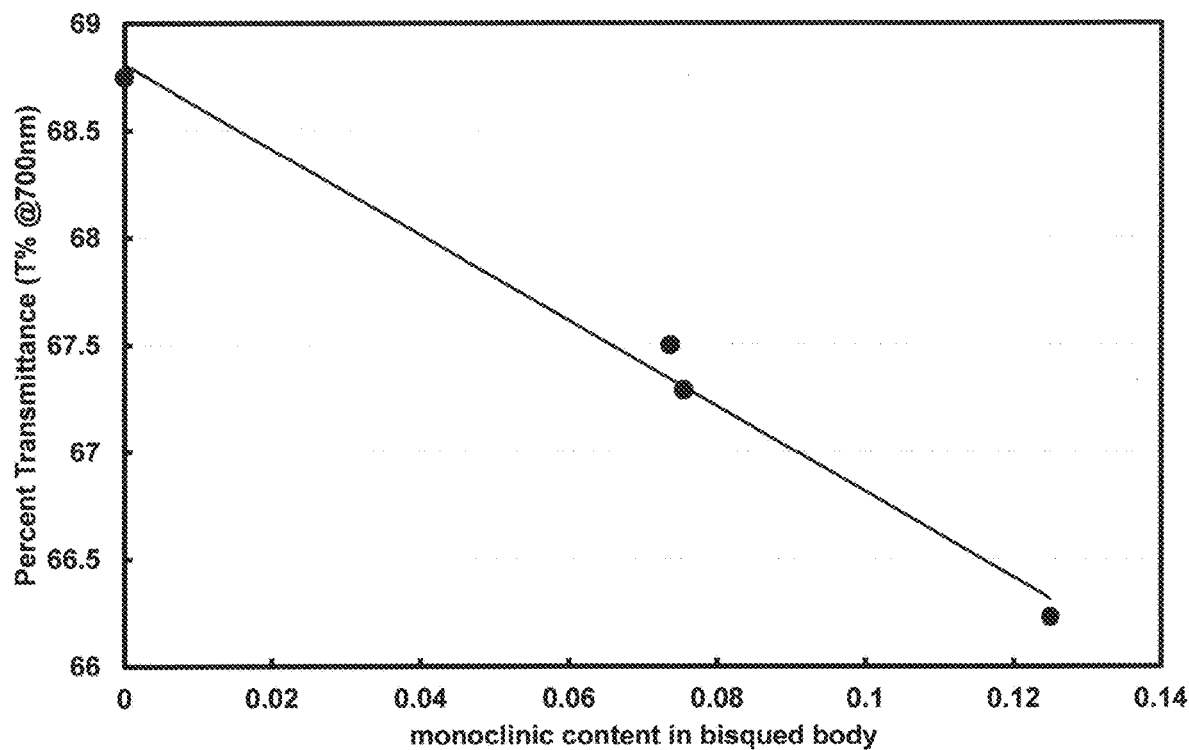
FIG. 8. Monoclinic Phase Content vs. Percent Transmittance Of 5.9 mol% Yttria-Stabilized Zirconia.

HIGHLY TRANSLUCENT ZIRCONIA MATERIAL, DEVICE, METHODS OF MAKING THE SAME, AND USE THEREOF

RELATED APPLICATIONS

This application claims the benefit of, and priority to U.S. Provisional Patent Application No. 62/721,340, filed Aug. 22, 2018, which is hereby incorporated by reference in its entirety.

BACKGROUND

Dental prosthetic devices, such as crowns, bridges, inlays, onlays, and veneers, are preferably formed from materials having good mechanical properties, including high flexural strength and high fracture toughness. In addition, these materials should preferably have a natural appearance in color, texture, translucency, and shape so that they are not readily distinguishable from the original natural teeth.

Ceramic materials, and particularly yttria-stabilized zirconia (YSZ), have been widely adopted for use in dental restorations because these materials have high strength and high fracture toughness. For example, U.S. Pat. No. 9,309,157 (assigned to Tosoh Corporation) describes zirconia sintered bodies for use in dental applications that are formed with yttria-stabilized zirconia powder, having 2 mol % to 4 mol % yttria as a stabilizer, and having reported three-point bending strength of 1,000 MPa or higher.

Conventional methods of manufacturing dental ceramic materials include molding a mixture of starting materials that includes yttria-stabilized zirconia powder into a green body, typically by press molding methods such as uniaxial pressing or cold isostatic pressing (CIP). In addition to the yttria-stabilized zirconia ceramic, starting materials for the conventional press molding methods may include a small amount (e.g., from 0 wt % to 0.25 wt % of the zirconia powder) of aluminum oxide ($Al_2O_3$) as an additive, and an organic binder (e.g., from 0.5 wt % to 10 wt %) to facilitate the press molding process. The green body can then be sintered at a sintering temperature of from 1450° C. to 1600° C. to obtain a zirconia sintered body.

US 2016/0310245 (also assigned to Tosoh Corporation) describes zirconia sintered bodies for use in dental applications that are formed from zirconia powder containing 4 mol % yttria to 6.5 mol % yttria, as a stabilizer. The '245 publication describes sintered bodies having total light transmittance of 37% to 40% to light at a wavelength of 600 nm. The International Organization for Standardization (ISO) specification of requirements for ceramic materials used in dentistry—ISO 6872:2015—requires that materials used for monolithic ceramic prostheses of up to 3 units should have a flexural strength of at least 500 MPa.

SUMMARY

Methods for enhancing properties, such as flexural strength, fracture toughness and/or translucency properties, of sintered, zirconia ceramic bodies and zirconia ceramic dental restorations are provided.

A method of making a ceramic green body may include dry forming processes, such as uniaxial pressing and cold isostatic pressing, and wet forming processes, including casting processes, such as slip-casting, vacuum casting, pressure casting, filter pressing, or centrifugal casting. In one embodiment, wet forming processes includes ceramic slip-casting processes using zirconia as a starting material of a ceramic slurry which is processed by a milling or grinding step. Ceramic slurry may be cast in a mold from which water is evacuated consolidating the solid material to form a ceramic green body.

A dental block is provided for producing a dental prosthesis. The dental block includes an yttria-stabilized zirconia green body having a density between 52% to 62% theoretical density and having an amount of yttrium oxide between 5 mol % and 8.5 mol %. In an embodiment, a zirconia green body has a median particle size of less than 350 nm, for example, where $D_{(50)}$ is from 150 nm to 350 nm, or 200 nm to 350 nm, such as, wherein $D_{(50)}$ is from 220 nm to 320 nm, or wherein $D_{(50)}$ is from 250 nm to 300 nm.

Methods are provided for heating zirconia ceramic green bodies in a pre-sintering process to form zirconia ceramic bisqued bodies having high densities and low porosities that are suitable for subtractive manufacturing processes such as machining, milling, and the like, that are suitable for use in forming dental restoration devices. Porous bisques bodies may be sintered by novel sintering methods, providing sintered bodies with enhanced physical properties.

In one embodiment, a dental block for producing a dental prosthesis comprises a zirconia bisqued body having a relative density between 55% and 65% of theoretical density. In some embodiments, the median pore size of bisque bodies is less than 200 nm, or less than 150 nm, less than 100 nm, such as between 40 nm and 80 nm, or between 45 nm and 75 nm, when measured according to the methods described herein.

In some embodiments, fully sintered ceramic bodies made from these ceramic powders having from 5.4 mol % yttria to 7.0 mol % yttria, have greater than 62 percent transmittance at 700 nm (when measured on a 1 mm thick sintered ceramic body). In other embodiments, fully sintered ceramic bodies made from these ceramic powders having between 5.5 mol % yttria and 6.9 mol % yttria, have greater than 65 percent transmittance at 700 nm (measured on a 1 mm thick fully sintered ceramic body). In further embodiments, sintered ceramic bodies made from these powders having between 5.7 mol % yttria and 6.3 mol % yttria, have greater than 68 percent transmittance at 700 nm, (when measured on a sintered 1 mm thick body by the methods described herein). In a further embodiment, the sintered yttria-stabilized zirconia ceramic materials have a flexural strength greater than or equal to, 300 MPa, or greater than or equal to, 500 MPa. In a further embodiment, fully sintered bodies having a flexural strength from 300 MPa to 750 MPA, may comprise an average grain size greater than or equal to 1 μm, such as from 1 μm to 30 μm, or from 1 μm to 15 μm, or greater than or equal to 8 μm, such as from 8 μm to 20 μm, when measured by the methods provided herein.

An unshaded zirconia sintered body is provided that comprises sintered yttria-stabilized zirconia ceramic material that has a total light transmittance value of at least 59% at 700 nm (for a 1 mm thick fully sintered ceramic body), such as between 59% and 78%, or between 590/and 75%, or between 59% and 73%, or between 59% and 71%, and a flexural strength greater than 500 MPa, that was made from yttria-stabilized zirconia ceramic material comprising at least 5 mol % yttria, or at least 5.2 mol % yttria, or at least 5.3 mol % yttria, or at least 5.4 mol % yttria, such as between 5 mol % yttria and 8 mol % yttria. or between 5.2 mol % yttria and 7.8 mol % yttria, or 5.4 mol % yttria and 7.5 mol % yttria.

In some embodiments, sintered yttria-stabilized zirconia ceramic materials may comprise at least 5.2 mol % yttria, and have a total light transmittance value of at least 60% at 700 nm (when a sintered 1 mm thick body of the ceramic material is measured at 700 nm) have flexural strength values greater than 300 MPa, or greater than 500 MPa, such as between 300 MPa and 750 MPa, or between 300 MPa and 600 MPa, or between 500 MPa and 750 MPa, or at least 600 MPa, or at least 625 MPa, or at least 650 MPa, or at least 700 MPa, or between 600 MPa and 750 MPa. The sintered yttria-stabilized zirconia ceramic materials may further comprise at least 5.3 mol % yttria or at least 5.5 mol % yttria, such as between 5 mol % yttria and 7.5 mol % yttria, or between 5.3 mol % yttria and 6.0 mol % yttria, or between 5.5 mol % yttria and 7.0 mol % yttria, or between 5.5 mol % yttria and 7.5 mol % yttria.

In some embodiments, sintered yttria-stabilized zirconia ceramic material having a total light transmittance at 700 nm (for a 1 mm thick fully sintered ceramic body) of greater than 62%, such as between 62% and 75%, such as between 62% and 73%, or between 62% and 71%, or between 62% and 69%, or between 63% and 75%, or between 64% and 75%, or between 64% and 73%, or between 64% and 71%, or between 65% and 75%, or between 65% and 73%, or between 68% and 75%. In these embodiments, the sintered yttria-stabilized zirconia ceramic materials may have flexural strength values greater than 500 MPa, such as between 500 MPa and 750 MPa, or at least 600 MPa, such as between 600 MPa and 750 MPa. In these embodiments, the sintered yttria-stabilized zirconia ceramic material may comprise at least 5 mol % yttria, such as at least 5.4 mol % yttria, or at least 5.5 mol % yttria, for example, between 5.5 mol % yttria and 6.0 mol % yttria, or between 5.5 mol % yttria and 7.0 mol % yttria, or between 5.5 mol % yttria and 7.5 mol % yttria.

In some embodiments, a zirconia ceramic body that has a total light transmittance value between 60% and 69%, or between 60% and 67%, or greater than 62%, such as between 62% and 69%, or between 62% and 67%, at 700 nm (for a 1 mm thick sample), may comprise an yttria-stabilized zirconia ceramic material having at least 6.5 mol % yttria, such as between 6.5 mol % yttria and 7.0 mol % yttria, or between 6.5 mol % yttria and 6.9 mol % yttria, and may have a flexural strength greater than 500 MPa.

In another embodiment, an unshaded zirconia sintered body that comprises sintered yttria-stabilized zirconia ceramic material having a total light transmittance value of at least 59% at 700 nm (for a 1 mm thick sample), a flexural strength greater than 500 MPa, made from yttria-stabilized zirconia ceramic material comprising at least 5.2 mol % yttria, such as between 5.4 mol % yttria and 7.5 mol % yttria, has a fracture toughness between 1.6 and 3.0 MPa·m$^{-1/2}$.

BRIEF DESCRIPTION OF THE FIGURE

FIGS. 5A through 5G. Graphical representations of bisque bodies by XRD analysis.

FIG. 6. Graphical representation of percent transmittance of several embodiments of sintered yttria-stabilized zirconia ceramic materials.

FIGS. 7A-7E. SEM of sintered yttria-stabilized zirconia ceramic body.

FIG. 8. Graphical representation of percent transmittance at 700 nm of sintered yttria-stabilized zirconia ceramic bodies vs. amount of monoclinic phase in bisque-stage zirconia ceramic material.

DETAILED DESCRIPTION

Figure 1A:
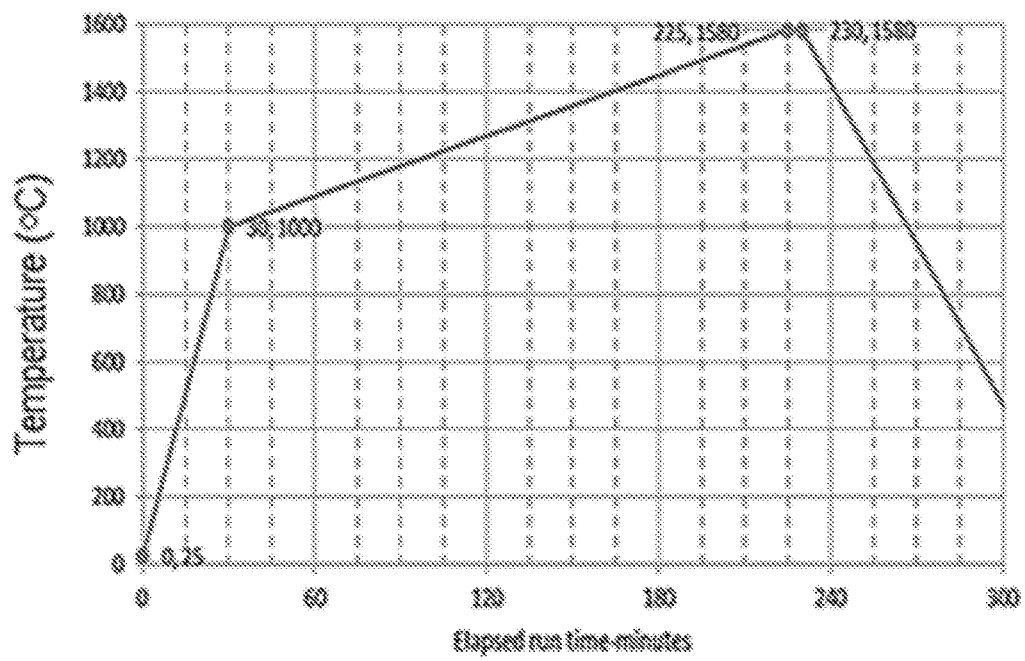
FIGS. 1A and 1B. Graphical representations of two embodiments of sintering profiles for sintering yttria-stabilized zirconia ceramic bodies.

Methods for making sintered ceramic bodies having high strength and translucency properties suitable for use as dental restorations are provided.

Method steps include processes for forming ceramic green bodies, bisque heating the green body to form a ceramic bisqued body, and sintering the bisqued body to obtain a ceramic sintered body. Methods also include one or more shaping processes, such as machining, milling or grinding, for shaping the ceramic material into a shaped body. The resulting ceramic sintered bodies have a combination of high strength and translucency desirable for forming dental restorations having high strength and esthetic properties comparable to those of natural teeth.

Green body manufacturing methods may include dry forming processes, such as uniaxial pressing and cold isostatic pressing, and wet forming processes, including but not limited to, slip-casting processes, pressure-casting, vacuum casting, filter pressing, and centrifugal casting methods. A green body manufacturing method such as a slip-casting process includes the steps of selecting starting materials; mixing and comminuting the starting materials to form a slurry; and casting the slurry to form a desired green body form, such as the shape of a milling block. Casting methods suitable for use herein include methods described in US Patent Publication 2009/0115084 published May 7, 2009, U.S. Pat. No. 9,434,651, issued Sep. 6, 2016, U.S. Pat. No. 9,365,459, issued Jun. 14, 2016, and US Patent Publication 2018/0235847, published Aug. 23, 2018, which are incorporated by reference herein, in their entireties.

Zirconia ceramic materials may be stabilized by 5 mol % to 8 mol % yttria. Starting materials for wet forming processes may include, but are not limited to, ceramic powder, dispersant, and deionized water to form ceramic slurries. Yttria-stabilized zirconia ceramic material in the slurry may comprise up to 7.5 mol % yttria, or up to 8.5 mol % yttria, for example, from 5 mol % yttria to 8.5 mol % yttria, from 5 mol % yttria to 8 mol % yttria, from 5 mol % yttria to 7.5 mol % yttria, 5 mol % yttria to 6.4 mol % yttria, from 5 mol % yttria to 5.6 mol % yttria, from 5.1 mol % yttria to 6.4 mol % yttria, from 5.2 mol % yttria to 7.5 mol % yttria, from 5.2 mol % yttria to 7.0 mol % yttria, from 5.4 mol % yttria to 7.5 mol % yttria, from 5.4 mol % yttria to 7.0 mol % yttria, from 5.5 mol % yttria to 7.5 mol % yttria, from 5.5 mol % yttria to 7 mol % yttria, from 5.5 mol % yttria to 6.9 mol % yttria, from 5.5 mol % yttria to 6 mol % yttria, from 5.5 mol % yttria to 5.9 mol % yttria, from 5.6 mol % yttria to 6.3 mol % yttria, from 5.7 mol % yttria to 6.3 mol % yttria, from 5.8 mol % yttria to 6.3 mol % yttria, from 6 mol % yttria to 8.5 mol % yttria, from 6 mol % yttria to 8 mol % yttria, from 6.0 mol % yttria to 7.5 mol % yttria, from 6 mol % yttria to 7 mol % yttria, from 6.0 mol % yttria to 6.8 mol % yttria, from 6.0 mol % yttria to 6.3 mol % yttria, from 6.2 mol % yttria to 7.5 mol % yttria, from 6.4 mol % yttria to 7.5 mol % yttria, from 7 mol % yttria to 8.5 mol % yttria, or from 7.2 mol % to 8.4 mol % yttria, to stabilize zirconia.

Yttria-stabilized zirconia ceramic material may be made from a mixture of one or more unstabilized zirconia and/or stabilized zirconia ceramic materials. The term stabilized zirconia ceramic herein includes fully stabilized and partially stabilized zirconia. For example, an yttria-stabilized zirconia ceramic material may be made from both unstabilized zirconia having no yttria or other stabilizer, and one or more yttria-stabilized zirconia ceramic materials, including, but not limited to, commercially available yttria-stabilized zirconia, for example, from Tosoh USA, such as Tosoh TZ-3YS and Tosoh TZ-PX430. The calculated amount of yttria (e.g., yttria mol %) in yttria-stabilized zirconia ceramic material may vary from 'nominal' values implied by commercial nomenclature (e.g. 3YS). The mol % yttria in zirconia ceramic material may be calculated, for example, based on compositional information received from manufacturer certification.

Zirconia ceramic materials used to prepare yttria-stabilized zirconia ceramic material mixtures include materials stabilized with 0 mol % yttria, 0.1 mol % to 2 mol % yttria, 2 mol % to 4 mol % yttria, 4 mol % to 6 mol % yttria, 5 mol % to 7 mol % yttria, 5 mol % to 7.5 mol % yttria, and 8 mol % to 10 mol % yttria. Yttria-stabilized zirconia ceramic materials suitable for use herein include mixtures of two or more zirconia ceramic materials stabilized with different amounts of yttria combined to obtain a total amount of yttria (mol %) in the zirconia ceramic material.

While not wishing to be bound by theory, it is believed that some mixtures of two or more zirconia ceramic materials may result in sintered yttria-stabilized zirconia ceramic bodies having enhanced properties compared to sintered bodies made from, for example, a single yttria-stabilized zirconia ceramic. Enhanced properties may include, for example, enhanced optical properties such as higher translucency (measured as percent transmittance at a specific wavelength) or higher flexural strength or fracture toughness, or a combination of more than one property.

In some embodiments, zirconia ceramic material mixtures comprise at least two zirconia ceramic materials, wherein at least one of the first and second zirconia ceramic materials is yttria-stabilized, or wherein both first and second zirconia ceramic materials are yttria-stabilized with different yttria concentrations. The first zirconia ceramic may be stabilized by an amount of yttria that is at least 0.5 mol % greater than a second zirconia ceramic material. In other embodiments, the amount of yttria of the first yttria-stabilized zirconia ceramic material is at least 1 mol % greater, or at least 2 mol % greater, or at least 3 mol % greater, or at least 4 mol % greater, or at least 5 mol % greater, than the second zirconia ceramic material.

Unstabilized and yttria-stabilized zirconia ceramic materials may be grouped by mol % yttria, for convenience, as group i) having from 7 mol % yttria to 10 mol % yttria, group ii) from 5 mol % yttria to 6 mol % yttria, and group iii) from 0 mol % yttria to 4 mol % yttria. When porous bisqued ceramic bodies formed from the yttria-stabilized zirconia ceramic mixtures are analyzed by XRD analysis, yttria-stabilized zirconia powders comprise one or more of monoclinic, cubic and tetragonal phases. In some embodiments, yttria stabilized zirconia powders of group i) having from 7 mol % yttria to 10 mol % yttria, comprise approximately 100% tetragonal and cubic phases, with greater than 80% as cubic phase, or greater than 50% as cubic phase, and less than or equal to 1% monoclinic phase, when bisqued ceramic bodies are measured by XRD. Yttria-stabilized zirconia powders of group ii) having from 5 mol % yttria to 6 mol % yttria, comprise at least 98% tetragonal and cubic phases combined, or at least 90% tetragonal and cubic phases when bisqued ceramic bodies are analyzed by XRD, and 10% or less, or 3% or less, or 2% or less, or 1% or less, of monoclinic phase. Yttria-stabilized zirconia powders of group iii) having from 0 mol % yttria to 4 mol % yttria, which may comprise monoclinic phase, may comprise no tetragonal or cubic phase, or less than 90% tetragonal and cubic phases, or less than 80% or less than 70% tetragonal and cubic phases, when bisqued ceramic bodies are analyzed by XRD analysis according to the method described herein.

In some embodiments, an yttria-stabilized zirconia ceramic material mixture comprises at least one zirconia ceramic materials from group i) having from 7 mol % yttria to 10 mol % yttria, comprising 100% tetragonal and cubic phases, with greater than 80% as cubic phase, or greater than 50% as cubic phase (when analyzed by XRD as a bisqued body), and at least one zirconia ceramic material from group ii) having from 5 mol % yttria to 6 mol % yttria, comprising at least 98% tetragonal and cubic phases, or at least 90% tetragonal and cubic phases (when analyzed by XRD as a bisqued body). In other embodiments, an yttria-stabilized zirconia ceramic material comprises at least one zirconia ceramic materials from group i) having from 7 mol % yttria to 10 mol % yttria, comprising 100% tetragonal and cubic phases, with greater than 80% as cubic phase, or greater than 50% as cubic phase (when analyzed by XRD as a bisqued body), and at least one zirconia ceramic material from group iii) having from 0 mol % yttria to 4 mol % yttria, comprising no tetragonal or cubic phase, or less than 90% tetragonal and cubic phases, or less than 80% or less than 70% tetragonal and cubic phases, (when analyzed by XRD as a bisqued body). In other embodiments, an yttria-stabilized zirconia ceramic material comprises at least one zirconia ceramic materials from group ii) having from 5 mol % yttria to 6 mol % yttria, comprising at least 98% tetragonal and cubic phases, or at least 90% tetragonal and cubic phases, (when analyzed by XRD as a bisqued body), and at least one zirconia ceramic material from group iii) having from 0 mol % yttria to 4 mol % yttria, comprising no tetragonal or cubic phase, or less than 90% tetragonal and cubic phases, or less than 80% or less than 70% tetragonal and cubic phases, (when analyzed by XRD as a bisqued body).

In another embodiment, an yttria-stabilized zirconia ceramic material mixture comprises at least two zirconia ceramic materials from group ii) each having from 5 mol % yttria to 6 mol % yttria, and comprising at least 98% tetragonal and cubic phases, or at least 90% tetragonal and cubic phases, wherein the difference in mol % yttria is at least 0.1 mol %, or wherein the difference in median particle size is at least 50 nm, between the at least two ceramic materials selected from group ii).

Zirconia ceramic bodies made by methods provided herein with material powders or powder mixtures may have lower amounts of monoclinic phase in the bisque stage and enhanced optical properties compared to materials with higher levels of monoclinic phase, while surprisingly achieving flexural strength greater than 300 MPa, or 500 MPa, when fully sintered. In some embodiments, zirconia ceramic powders or powder mixtures comprising a median powder particle size where D(50) is less than 500 nm, or less than 400 nm, or less than 300 nm or less than 250 nm, or less than 80 nm, or between 40 nm and 300 nm, after wet processing by the methods described herein, comprise at least 70% tetragonal and cubic phases, or at least 80% tetragonal and cubic phases, or at least 90% tetragonal and cubic phases, or at least 95% tetragonal and cubic phases. In other embodiments, bisqued bodies have at least 98% tetragonal and cubic phases and less than or equal to 2% monoclinic phase, or at least 99% tetragonal and cubic phases and less than or equal to 1% monoclinic phase, or at least 99.5%, tetragonal and cubic phases, and less than or equal to 0.5% monoclinic phase, when measured on bisqued bodies having a hardness less than 0.9 GPa.

Yttria-stabilized zirconia ceramic materials used as starting materials may optionally include a small amount of alumina (aluminum oxide, $Al_2O_3$) as an additive. For example, some commercially available yttria-stabilized zirconia ceramic material include alumina at concentrations of from 0 wt % to 2 wt %, or from 0 wt % to 0.25 wt %, such as 0.1 wt %, relative to the zirconia material. Optional additives such as alternative stabilizer materials, such as cerium oxide and/or magnesium oxide may be added to the zirconia ceramic material. Still other optional additives include grain growth inhibitors, sintering aids, and/or toughening aids.

Coloring agents also may be added directly to the ceramic powder to create shaded sintered zirconia ceramic materials having dentally acceptable shades after sintering to theoretical density. As used herein, unshaded zirconia ceramic materials refer to materials in which no coloring agent has been added, and unshaded zirconia ceramic materials often have a bright white appearance conventionally considered esthetically unsuitable for use as a dental restoration without the addition of further coloring or staining. Shaded zirconia ceramic materials comprise additives that may include, but are not limited to metal-containing oxides, salts, or other compounds or complexes that include erbium (Er), terbium (Tb), chromium (Cr), cobalt (Co), iron (Fe), manganese (Mn), nickel (Ni), praseodymium (Pr), copper (Cu), and/or other coloring metal ions in an amount to obtain desired dental shades in final sintered restorations. In some embodiments, shaded yttria-stabilized zirconia ceramic material that has been sintered to approximately full theoretical density match a shade tab from a Vita A1-D4® Classical Shades shade guide or Vita Bleached Shades shade guide, such as 0M1, 0M2 or 0M3 bleach shades, (available through Vita North America) when measured according to the shade match evaluation test method provided herein. In some embodiments, coloring compositions may be applied to the ceramic body after formation of the green, bisque or sintered ceramic body, and may comprise a coloring agent having at least one metal included, but not limited to, Tb, Er, Cr, Fe, Mn, Ni, Pr, Cu or Co, and combinations thereof. In some embodiments, the amount of coloring agent in a sintered ceramic body may be from 100 ppm to about 2000 ppm, or 200 ppm to 1500 ppm, (measured as metal ion) per gram of the yttria-stabilized zirconia ceramic material. Other esthetic additives may be included to obtain desired opalescence or fluorescence properties for dental applications.

Dispersants used to form ceramic suspensions or ceramic slurries to form green bodies by slip-casting manufacturing methods such as those described herein, function by promoting the dispersion and/or stability of the slurry and/or decreasing the viscosity of the slurry. Dispersion and deagglomeration may occur through electrostatic, electrosteric, or steric stabilization. Examples of suitable dispersants include nitric acid, hydrochloric acid, citric acid, diammonium citrate, triammonium citrate, polycitrate, polyethyleneimine, polyacrylic acid, polymethacrylic acid, polymethacrylate, polyethylene glycols, polyvinyl alcohol, polyvinyl pyrillidone, carbonic acid, and various polymers and salts thereof. These materials may be either purchased commercially, or prepared by known techniques. Specific examples of commercially available dispersants include Darvan® 821-A ammonium polyacrylate dispersing agent commercially available from Vanderbilt Minerals, LLC; Dolapix™ CE 64 organic dispersing agent and Dolapix™ PC 75 synthetic polyelectrolyte dispersing agent commercially available from Zschimmer & Schwarz GmbH; and Duramax™ D 3005 ceramic dispersant commercially available from Dow Chemical Company.

Zirconia ceramic and dispersant starting materials added to deionized water may be mixed to obtain a slurry. Slurries may be subjected to a comminution process for mixing, deagglomerating and/or reducing particle size of zirconia ceramic powder particles. Comminution may be performed using one or more milling process, such as attritor milling, horizontal bead milling, ultrasonic milling, or other milling or comminution process, such as high shear mixing or ultra-high shear mixing capable of reducing zirconia ceramic powder particle sizes described herein.

In one embodiment, a zirconia ceramic slurry may undergo comminution by a horizontal bead milling process. Media may comprise zirconia-based beads, for example, having a diameter of 0.4 mm. A suspension or slurry having a zirconia ceramic solids loading of about 70 wt % to about 80 wt % and a dispersant concentration from 0.004 gram dispersant/gram zirconia ceramic powder to 0.01 gram dispersant/gram zirconia ceramic powder, may be used to prepare the zirconia ceramic slurry. Milling processes may include, for example, a flow rate of 1 kg to 10 kg zirconia ceramic powder/hour, such as, approximately 6 kg zirconia ceramic powder/hour where, for example, approximately 6 kg of zirconia ceramic material is milled for approximately one hour, at a mill speed of approximately 1500 rpm to 3500 rpm, for example, approximately 2000 rpm.

In some embodiments, where commercially available zirconia ceramic is used as starting materials to prepare the ceramic slurry, the measured median particle size, or particle size distribution at $D_{(50)}$ may be about 200 nm to 600 nm, or greater than 600 nm, which includes agglomerations of particles of crystallites having a crystallite size of about 20 nm to 40 nm. As used herein, the term "measured particle size" refers to measurements obtained by a Brookhaven Instruments Corp. X-ray disk centrifuge analyzer. By processes described herein, an initial particle size distribution at, for example, a $D_{(50)}$ of about 200 nm to 600 nm, or greater than 600 nm, may be reduced to provide a zirconia ceramic material contained in a slurry having a median particle size where $D_{(50)}$ is from 100 nm to 600 nm, such as, wherein $D_{(50)}$ is from 150 nm to 350 nm, or from 220 nm to 320 nm or wherein $D_{(50)}$ is from 250 nm to 300 nm. In some embodiments, after comminution processes ceramic slurries comprise particle size distributions wherein $D_{(10)}$ is from 100 nm to 250 nm, or $D_{(10)}$ is from 120 nm to 220 nm, or $D_{(10)}$ is from 120 nm to 200 nm, and $D_{(90)}$ of zirconia particles is less than 800 nm, or $D_{(90)}$ is in the range of 250 nm to 425 nm.

By processes described herein, zirconia ceramic material may comprise an initial median particle size, for example, a $D_{(50)}$ of less than 250 nm, which upon comminution may provide a slurry comprising a zirconia ceramic material having a median particle size where $D_{(50)}$ is from 100 nm to 250 nm, such as, wherein $D_{(50)}$ is from 125 nm to 225 nm. Yttria-stabilized zirconia ceramic material comprising mixtures of two or more yttria stabilized zirconia ceramic materials each having different initial median particle sizes, may be comminuted as a mixture in a slurry by the processes described herein. Reduced particle sizes and/or narrow ranges of comminuted zirconia ceramic material, in combination with the dispersants describe above, may provide cast parts with a higher density and smaller pores that form sintered bodies having higher translucency and/or strength than those obtained by way of conventional pressing and slip-casting processes.

Zirconia ceramic slurries may be cast into a desired shape, such as a solid block, disk, near net shape, or other shape. Ceramic slurries may be poured into a porous mold (e.g., plaster of paris or other porous/filtration media) having the desired shape, and cast, for example, under the force of capillary action, vacuum, pressure, or a combination thereof (for example, by methods provided in US 2013/0313738, which is hereby incorporated by reference in its entirety). Green bodies may form a desired shape as water contained in the slurry is absorbed/filtered through the porous media. Excess slurry material, if any remaining, may be poured off the green body. Green bodies removed from molds may dry, for example, at room temperature in a controlled, low humidity environment. Dental milling blanks may be cast, for example, as a solid block, disk or near-net-shape, having dimensions suitable for use in milling or grinding single unit or multi-unit restorations, such as crowns, veneers, bridges, partial or full-arch dentures, and the like.

Manufacturing processes described herein may provide green bodies having relative densities $\rho_R$ greater than 52%, such as from 52% to 65% relative density, or such as from 56% to 62% relative density. As used herein, the term "relative density" ($\rho_R$) refers to the ratio of the measured density $\rho_M$ of a sample (g/cm³) to the theoretical density $\rho_T$ for the zirconia ceramic material, provided in Table 1, (i.e., $\rho_R=\rho_M/\rho_T$).

Green bodies may be partially consolidated to obtain bisqued bodies by a heating step. Bisquing methods include heating or firing green bodies, such as green bodies in the shape of blocks to obtain, for example, porous bisqued blocks. In some embodiments, relative densities of bisque blocks do not increase more than 5% over the green body density. In some embodiments, the ceramic bodies are bisque heated so that the difference between the relative densities of the bisque body and the green body is 3% or less. Resulting bisqued bodies may be fully dried and have strength sufficient to withstand packaging, shipping, and milling, and in some embodiments, have a hardness value of less than or equal to 0.9 GPa, when tested by the hardness test method described herein. Bisque firing steps may include heating the green body at an oven temperature of from 800° C. to 1100° C. for a holding period of about 0.25 hours to 3 hours, or about 0.25 hours to 24 hours, or by other known bisquing techniques. In some embodiments, bisque processes comprise heating green bodies in an oven heated at an oven temperature of 900° C. to 1000° C. for 30 minutes to 5 hours.

Processes described herein may provide a bisqued body having a relative density $\rho_R$ greater than or equal to 55%, such as from 55% to 65%, or from 58% to 62%, or from 59% to 62%. Bisqued bodies may have a porosity of less than or equal to 45%, such as from 35% to 45%, or from 38% to 42%, or from 38% to 41%. As used herein, the term "porosity", expressed as percent porosity above, is calculated as: percent porosity=1−percent relative density. A dental block for producing a dental prosthesis includes a zirconia bisqued body having a density of between 56% to 65% of theoretical density and having a porosity of between 35% and 44%, such as between 38% and 41%.

In some embodiments, the median pore size of bisque bodies is less than 200 nm, or less than 150 nm, less than 100 nm, such as from 35 nm to 90 nm, or from 35 nm to 40 nm, or from 40 nm to 80 nm, or from 40 nm to 70 nm, or from 45 nm to 75 nm, or from 45 nm to 50 nm, or from 50 nm to 80 nm, or from 50 nm to 75 nm, or from 55 nm to 80 nm, or from 55 nm to 75 nm, when measured according to the methods described herein. As used herein, the term "median pore diameter" refers to the pore diameter measurements obtained from a bisqued body via mercury intrusion performed with an Autopore V porosimeter from Micromeritics Instrument Corp.

Conventional subtractive processes, such as milling or machining processes known to those skilled in the art, may be used to shape a bisqued zirconia ceramic body or milling block into a pre-sintered dental restoration. For dental applications, a pre-sintered restoration may include a dental restoration such as a crown, a multi-unit bridge, an inlay or onlay, a veneer, a full or partial denture, or other dental restoration. For example, bisque stage blocks milled to form bisque-stage dental restorations having anatomical facial surface features including an incisal edge or biting surface, anatomical dental grooves and cusps, and are sintered to densify the bisque-stage restoration into the final dental restoration that may permanently installed in the mouth of a patient. In alternative embodiments, bisque-stage zirconia ceramic bodies are shaped into near-net-shape blocks having generic sizes and shapes that are sintered to theoretical density prior to machining into a final patient-specific dental restoration. The sintered near-net-shape bodies may be prepared having a shape and/or size that is suitable for range of similarly sized and shaped final restoration products.

Bisqued bodies or pre-sintered parts may be "fully sintered" under atmospheric pressure to achieve a density that is at least 98% of the theoretical density of a sintered body. Ceramic bodies that are tested, for example, for flexural strength and translucency (measured as percent transmittance) are 'fully sintered' to 98% to 100%, of theoretical density.

Bisqued, or pre-sintered, bodies, may be "fully sintered" under atmospheric pressure by sintering to a density that is at least 98% of the theoretical density of the ceramic material. Sintering temperature ranges may include oven temperatures greater than or equal to 1200° C., such as from 1200° C. to 1700° C., or from 1200° C. to 1680° C., or from 1200° C. to 1650° C., from 1200° C. to 1600° C., or from 1400° C. to 1580° C., or from 1400° C. to 1450° C., or from 1600° C. to 1700° C., or from 1620° C. to 1680° C., or from 1630° C. to 1670° C. Sintering profiles may include one or more optional hold times (dwell times) at a temperature within a sintering temperature range, such as a hold time from 1 minute to 48 hours, such as from 10 minutes to 5 hours, or from 10 minutes to 3 hours, or from 30 minutes to 4 hours, or from 1 hour to 4 hours, or from 1 hour to 3 hours, or from 2 hours to 2.5 hours.

Figure 1B:
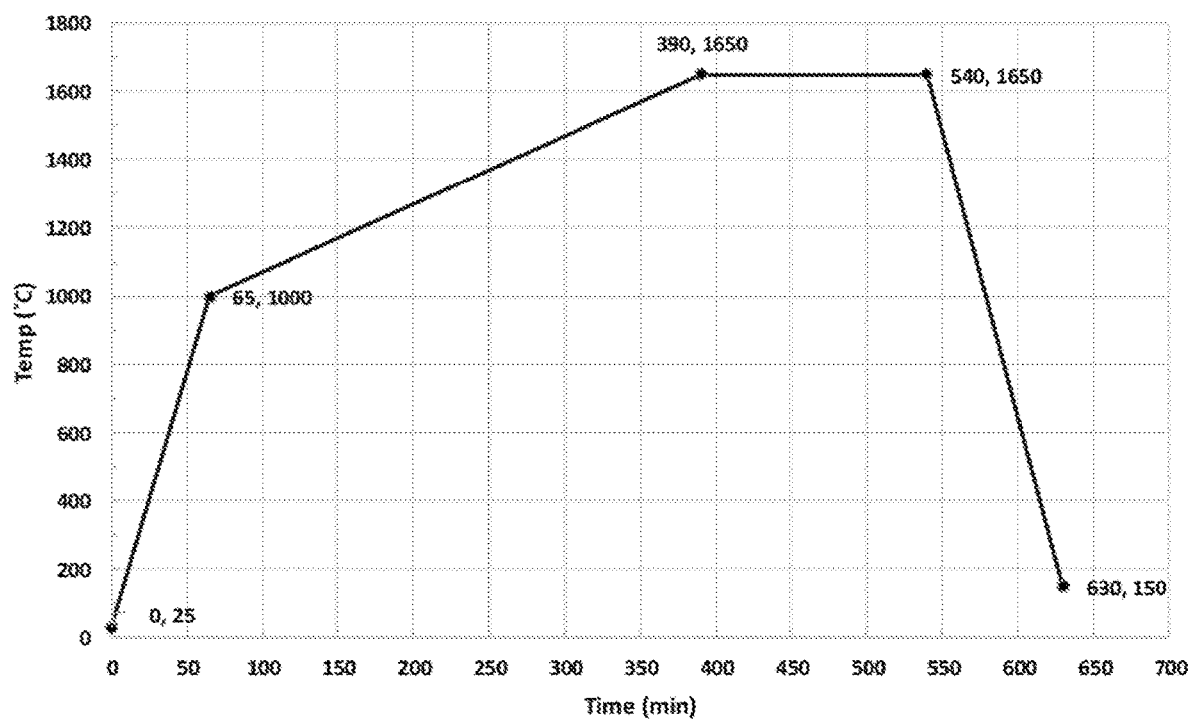

In other embodiments, multi-step sintering processes are provided that comprise a temperature gradient to reach an oven temperature at or above 1200° C., such as, from 1200° C. to 1650° C., or from 1200° C. 1700° C. As illustrated in FIG. 1A. a sintering profile is provided having a gradient between 1000° C. and a peak oven temperature of 1580° C., and FIG. 1B having a gradient to a peak oven temperature of 1650° C.

Figure 2:
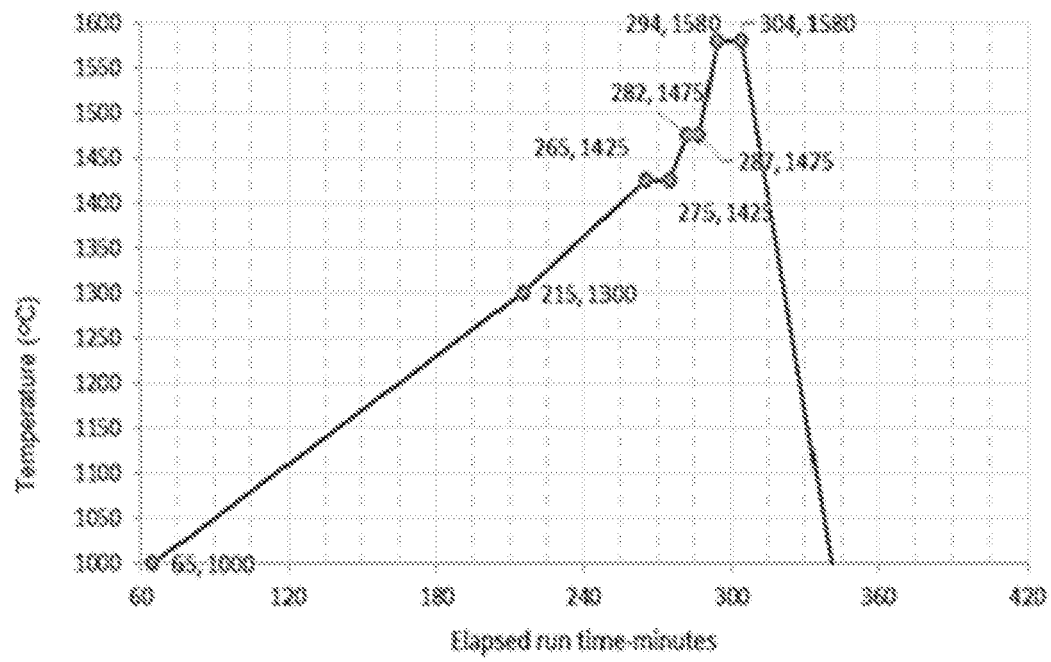
FIG. 2. A graphical representation of one embodiment of a sintering profile suitable for sintering yttria-stabilized zirconia ceramic bodies.

Multi-step sintering processes may have one or more temperature gradients within a sintering temperature range, each gradient having the same or different ramp rate to reach a temperature at or above 1200° C., as illustrated in FIG. 2, having three gradients between 1300° C. and 1580° C., each having an optional hold time of 0 minutes to 10 minutes. Sintering methods may optionally having no hold time at a sintering temperature, or one hold time, or multiple hold times at an oven temperature at or above 1200° C., as illustrated in FIG. 2, FIG. 3A, FIG. 3B and FIG. 4.

Figure 3A:
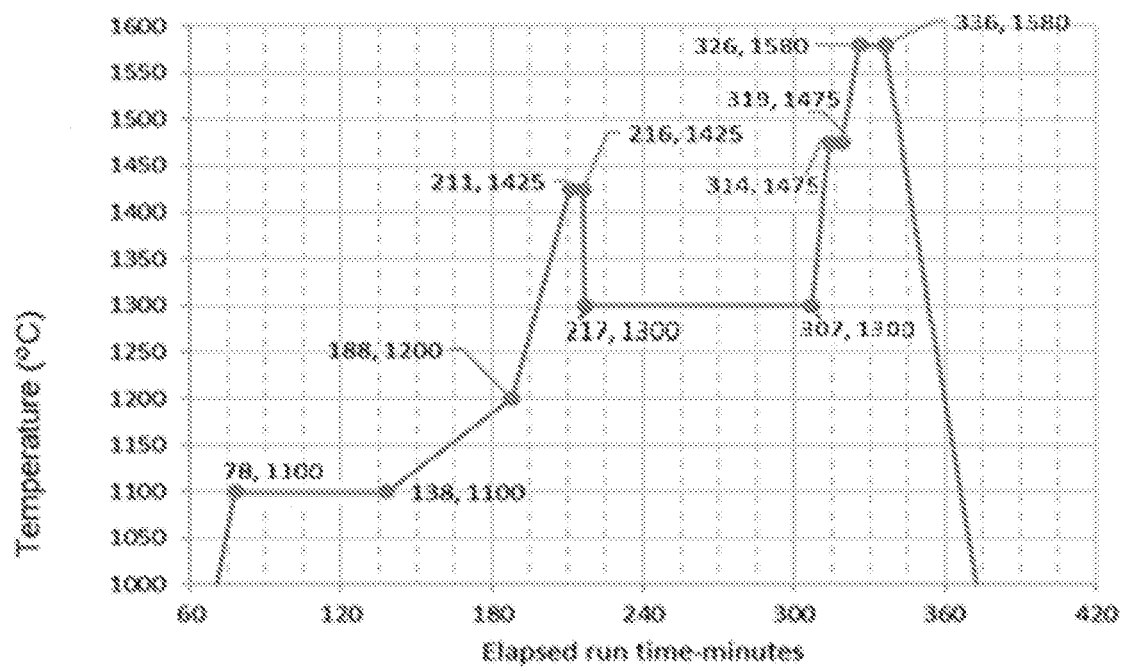
FIGS. 3A and 3B. Graphical representations of embodiments of sintering profiles suitable for sintering yttria-stabilized zirconia ceramic bodies.

Multi-step sintering processes may comprise a heating profile having a temperature peak at or above 1200° C. (having a hold times between 0 minutes and 20 minute) that is adjacent a lower temperature having a hold time at the lower temperature of at least 2 minutes. A sintering profile may comprise multiple temperature peaks at or above 1200° C. and at least one temperature step that is from 25° C. to 600° C. lower, or from 50° C. to 400° C. lower, than a preceding or subsequent temperature peak above 1200° C. For example, as illustrated in FIG. 3A, a sintering profile comprises two temperature peaks (at 1425° C. and 1475° C.) and a lower temperature step of 1300° C. there between. A lower temperature step between two higher temperature peaks may have a hold time between 2 minutes and 5 hours, such as in FIG. 3A wherein a lower temperature step at 1300° C. has a hold time of 20 minutes. As exemplified in the multi-step sintering process of FIG. 3B, two temperature peaks (at 1450° C. and 1650° C.) may be separated by a lower temperature step at 1200° C. having a hold time of 90 minutes. In some embodiments, in a multi-step sintering process, a first temperature peak may have a hold time of 0 to 20 minutes, and a final temperature peak may have a hold time from 0 minutes to 5 hours.

White, unshaded zirconia sintered bodies obtained by the processes described herein demonstrate combinations of high translucency at identified wavelengths (e.g., 700 nm, for 1 mm thick sintered body), and high flexural strength values that have not been achieved by zirconia sintered bodies having similar yttria concentrations that have been manufactured by conventional manufacturing methods.

An unshaded zirconia sintered body is provided that is made from slip-casting processes described herein. A ceramic body comprises sintered yttria-stabilized zirconia ceramic material that has a total light transmittance value of at least 59% at 700 nm (measured on a 1 mm thick fully sintered ceramic body), such as between 59% and 75%, or between 59% and 72%, or between 59% and 71%, and a flexural strength greater than 500 MPa, was made from yttria-stabilized zirconia ceramic material comprising at least 5.2 mol % yttria, or at least 5.3 mol % yttria, or at least 5.4 mol % yttria, such as between 5.2 mol % yttria and 7.5 mol % yttria, or between 5.4 mol % yttria and 7.5 mol % yttria, or between 5.4 mol % yttria and 6.9 mol % yttria.

In some embodiments, the sintered yttria-stabilized zirconia ceramic material having a total light transmittance value of at least 59% at 700 nm, such as between 59%0 and 75%, or between 60% and 75%, having at least 5.3 mol % yttria, such as between 5.3 mol % yttria and 7.0 mol % yttria, or at least 5.4 mol % yttria, such as between 5.4 mol % yttria and 6.5 mol % yttria, has a flexural strength greater than or equal to 550 MPa, or greater than or equal to 600 MPa, or greater than or equal to 650 MPa, or greater than or equal to 700 MPa, such as between 600 MPa and 750 MPa, or between 650 MPa and 750 MPa, when tested according to the methods described herein. In some alternative embodiments, a zirconia ceramic body having a total light transmittance value of at least 59%, such as between 59% and 75%, or between 60% and 72%, at 700 nm (measured on a 1 mm thick fully sintered ceramic body), comprising an yttria-stabilized zirconia ceramic material having at least 5.2 mol % yttria, or at least 5.3 mol % yttria, or at least 5.5 mol % yttria, such as between 5.5 mol % yttria and 7.0 mol % yttria, or between 5.5 mol % yttria and 6.9 mol % yttria, may also have a total light transmittance value of at least 50%, such as between 50% and 65%, or between 50% and 62%, at 500 nm (measured on a 1 mm thick fully sintered ceramic body), and may have a flexural strength greater than 500 MPa.

A ceramic body comprises sintered yttria-stabilized zirconia ceramic material that has a total light transmittance value of at least 60%, or at least 62%, or at least 63%, or at least 64% or at least 65% or at least 66% or at least 67% or at least 68% or at least 69%, or at least 70%, or at least 71%, or at least 73%, or at least 74%, or at least 75%, at 700 nm (measured on a 1 mm thick fully sintered ceramic body). In some embodiments, these sintered yttria-stabilized zirconia ceramic materials having a total light transmittance value of at least 60% at 700 nm (measured on a 1 mm thick fully sintered ceramic body) have flexural strength values greater than 500 MPa, such as between 500 MPa and 750 MPa, or at least 600 MPa, or at least 625 MPa, or at least 650 MPa, or at least 700 MPa, or between 600 MPa and 750 MPa.

In other embodiments, a ceramic body comprises sintered yttria-stabilized zirconia ceramic material that has a total light transmittance value of at least 60%, or at least 62%, such as between 62% and 75%, at 700 nm (measured on a 1 mm thick fully sintered ceramic body), and has a flexural strength value greater than 500 MPa, such as between 500 MPa and 750 MPa, or at least 600 MPa, such as between 600 MPa and 750 MPa. The ceramic body according to this embodiment, may comprise an yttria-stabilized zirconia ceramic material having at least 5.3 mol % yttria, such as between 5.3 mol % yttria and 7.5 mol % yttria, or between 5.5 mol % yttria and 7.0, or between 5.5 mol % yttria and 6.5 mol % yttria. Or, in an alternative embodiment, the ceramic body comprising a total light transmittance value greater than 60%, such as between 60% and 69%, or between 60% and 67%, or greater than 62%, such as between 62% and 69%, or between 62% and 67%, at 700 nm (measured on a 1 mm thick fully sintered ceramic body), comprises at least 6.5 mol % yttria, such as between 6.5 mol % yttria and 7.0 mol % yttria, or between 6.5 mol % yttria and 6.9 mol % yttria, and, optionally, may have a flexural strength greater than 500 MPa.

Some embodiments of ceramic bodies comprising sintered yttria-stabilized zirconia ceramic material have a total light transmittance at 700 nm (measured on a 1 mm thick fully sintered ceramic body) of greater than 62%, such as between 62% and 75%, such as between 62% and 73%, or between 62% and 71%, or between 62% and 69%, or between 63% and 75%, or between 64% and 75%, or between 64% and 73%, or between 64% and 71%, or between 65% and 75%, or between 65% and 73%, or between 68% and 75%. In these embodiments, the sintered yttria-stabilized zirconia ceramic materials may have flexural strength values greater than 500 MPa, such as between 500 MPa and 750 MPa, or at least 600 MPa, such as between 600 MPa and 750 MPa. In these embodiments, the sintered yttria-stabilized zirconia ceramic material may comprise at least 5.4 mol % yttria, such as, between 5.5 mol % yttria and 6.0 mol % yttria, or between 5.5 mol % yttria and 7.0, or between 5.5 mol % yttria and 7.5 mol % yttria.

In some embodiments, a zirconia ceramic body that has a total light transmittance value between 62% and 75%, or between 62% and 73%, or between 62% and 71%, at 700 nm (measured on a 1 mm thick fully sintered ceramic body), may comprise an yttria-stabilized zirconia ceramic material having between 5.4 mol % yttria and 7.0 mol % yttria, or between 5.7 mol % yttria and 6.3 mol % yttria, and may have a flexural strength greater than 500 MPa, such as, greater than 600 MPa, or greater than 625 MPa, or between 600 MPa and 750 MPa. In other embodiments, the zirconia ceramic bodies may comprise between 5.4 mol % yttria and 6.0 mol % yttria, or between 5.6 mol % yttria and 6.3 mol % yttria, and may have a total light transmittance value between 62% and 75%, and a flexural strength greater than 600 MPa, such as, greater than 625 MPa, or between 600 MPa and 750 MPa.

In some embodiments, a zirconia ceramic body that has a total light transmittance value of at least 63%, such as between 63% and 73%, or between 63% and 71%, or at least 64%, such as between 64% and 73%, at 700 nm (measured on a 1 mm thick fully sintered ceramic body), may comprise an yttria-stabilized zirconia ceramic material having between 5.5 mol % yttria and 7.0 mol % yttria, or between 5.6 mol % yttria and 6.5 mol % yttria, between 5.6 mol % yttria and 6.1 mol % yttria, and may have a flexural strength greater than 500 MPa, such as, greater than 600 MPa, or greater than 625 MPa, or between 600 MPa and 750 MPa.

In some embodiments, a zirconia ceramic body that has a total light transmittance value of at least 65%, or at least 66%, or between 65% and 75%, or between 65% and 71%, at 700 nm (measured on a 1 mm thick fully sintered ceramic body), may comprise an yttria-stabilized zirconia ceramic material having at least 5.6 mol % yttria, such as between 5.6 mol % yttria and 6.7 mol % yttria, or between 5.9 mol % yttria and 6.5 mol % yttria, and may have a flexural strength greater than 500 MPa, such as, greater than 600 MPa, or between 500 MPa and 750 MPa.

In some embodiments, a zirconia ceramic body that has a total light transmittance value of at least 68%, such as between 68% and 75%, or between 68% and 73%, at 700 nm (measured on a 1 mm thick fully sintered ceramic body), may comprise an yttria-stabilized zirconia ceramic material having at least 5.7 mol % yttria, such as between 5.7 mol % yttria and 6.3 mol % yttria, or between 5.8 mol % yttria and 6.3 mol % yttria, or between 5.8 mol % yttria and 6.1 mol % yttria, or between 6.0 mol % yttria and 6.3 mol % yttria, and may have a flexural strength greater than 500 MPa, such as, greater than 550 MPa, or greater than 600 MPa, or between 500 MPa and 750 MPa.

In another embodiment, an unshaded zirconia sintered body that comprises sintered yttria-stabilized zirconia ceramic material having a total light transmittance value of at least 59% at 700 nm (measured on a 1 mm thick fully sintered ceramic body), such as between 60% and 75%, or between 60% and 70%, a flexural strength greater than or equal to 500 MPa, made from yttria-stabilized zirconia ceramic material comprising at least 5.2 mol % yttria, such as between 5.4 mol % yttria and 7.5 mol % yttria, or between 5.4 mol % yttria and 6.5 mol % yttria, has a fracture toughness value between 1.6 MPa·m$^{-1/2}$ and 3.0 MPa·m$^{-1/2}$, or between 1.7 MPa·m$^{-1/2}$ and 3.0 MPa·m$^{-1/2}$, or between 1.7 MPa·m$^{-1/2}$ and 2.5 MPa·m$^{-1/2}$, or between 1.7 MPa·m$^{-1/2}$ and 2.3 MPa·m$^{-1/2}$, or between 1.7 MPa·m$^{-1/2}$ and 2.1 MPa·m$^{-1/2}$, or between 1.7 MPa·m$^{-1/2}$ and 2.0 MPa·m$^{-1/2}$.

Yttria-stabilized zirconia ceramic materials provided herein that have been sintered to full density by sintering profiles having an oven temperature greater than 1600° C., may have even further enhanced properties. In some embodiments, yttria-stabilized zirconia ceramic bodies comprising between 5 mol % and 7.2 mol % yttria, have a transmittance greater than 62%, such as between 63% and 77% transmittance, or between 63% and 72% at 700 nm (when measured as a 1 mm thick ceramic body sintered to theoretical density), while maintaining a flexural strength greater than or equal to 500 MPa. The sintered zirconia ceramic bodies may further comprise a fracture toughness greater than 1.5 MPa·m$^{-1/2}$. In some embodiments, the sintered ceramic body has an average grain size between 1 and 30 µm, or between 1 and 20 µm, or between 1 and 15 µm.

Other sintered zirconia ceramic bodies may be stabilized with between 5.1 mol % and 7.1 mol % yttria, and may comprise a transmittance between 63% and 77%, at 700 nm (when measured on a fully sintered ceramic body having a 1 mm thickness). In another embodiment, the sintered zirconia ceramic body may be stabilized with between 5.2 mol % and 7 mol % yttria, or between 5.8 mol % and 6.3 mol % yttria, and comprise a transmittance between 63% and 77% at 700 nm. In some embodiments, sintered zirconia ceramic bodies, stabilized with between 5.8 mol % and 6.3 mol % yttria, may comprise a transmittance between 63% and 74% at 700 nm and a fracture toughness value greater than 2 MPa·m$^{-1/2}$. In another embodiment, sintered zirconia ceramic bodies, stabilized with between 5.2 mol % and 7.2 mol % yttria, may comprise a transmittance between 63% and 72% at 700 nm, and a flexural strength greater than or equal to 550 MPa.

In further embodiments, upon sintering at oven temperatures greater than 1600° C., a yttria-stabilized zirconia ceramic body comprising the ceramic materials provided herein, comprising between 5 mol % and 6.4 mol % yttria, may have a transmittance greater than 62% at 700 nm (when measured on a 1 mm thick ceramic body sintered to theoretical density), and a flexural strength greater than 500 MPa. In other embodiments, a sintered zirconia ceramic body stabilized with 5 mol % and 5.6 mol % yttria, has a transmittance between 62% and 68% at 700 nm (when shaped as a 1 mm thick body sintered to theoretical density), and a flexural strength greater than 550 MPa. In still other embodiments, a sintered zirconia ceramic body stabilized with 5.1 mol % and 5.5 mol % yttria, has a transmittance between 62% and 73% at 700 nm (when shaped as a 1 mm thick body sintered to theoretical density), and a flexural strength greater than or equal to 550 MPa, such as between 550 MPa and 750 MPa. In still further embodiments, a sintered zirconia ceramic body stabilized with 5.1 mol % and 6.4 mol % yttria, has a transmittance between 68% and 78%, or between 68% and 75%, or between 62% and 70%, between 64% and 70%, at 700 nm (when measured on a 1 mm thick ceramic body sintered to theoretical density), and a flexural strength greater than or equal to 500 MPa, such as between 500 MPa and 750 MPa, or between 500 MPa and 700 MPa.

In other embodiments, upon sintering at oven temperatures greater than 1600° C., a yttria-stabilized zirconia ceramic body comprising between 6.2 mol % and 7.6 mol % yttria, has a transmittance greater than 55%, such as between 55% and 74%, at 700 nm (when measured on a 1 mm thick ceramic body sintered to theoretical density). In some embodiments, the sintered zirconia body has a flexural strength greater than 300 MPa, or greater than or equal to 500 MPa. In still other embodiments, the yttria-stabilized zirconia ceramic body comprises between 6.2 mol % and 7.4 mol % yttria, a transmittance between 62% and 74%, at 700 nm (when measured on a 1 mm thick ceramic body sintered to theoretical density), and a flexural strength greater than 300 MPa, or, where the zirconia ceramic body comprises between 6.4 mol % and 7.2 mol % yttria, it may further have a flexural strength greater than 500 MPa. In further embodiments, the yttria-stabilized zirconia ceramic body comprises between 6.2 mol % and 6.8 mol % yttria, and has a transmittance between 62% and 74%, at 700 nm (when measured on a 1 mm thick ceramic body sintered to theoretical density), and, optionally, a flexural strength greater than 500 MPa.

In still other embodiments, the yttria-stabilized zirconia ceramic body comprises between 6.4 mol % and 7.6 mol % yttria, a transmittance between 55% and 63%, at 700 nm (when measured on a 1 mm thick body sintered to theoretical density), and a flexural strength greater than 300 MPa, In still other embodiments, the yttria-stabilized zirconia ceramic body comprises between 7 mol % and 8.5 mol % yttria, a transmittance between 50% and 62%, or between 55% and 62%, or between 57% and 62%. at 700 nm (when shaped as a 1 mm thick body sintered to theoretical density), and, optionally, a flexural strength greater than 300 MPa.

In a further embodiment, shaded sintered yttria-stabilized zirconia ceramic bodies may be prepare, which upon milling and/or sintering, form a final dental restoration having a dentally acceptable shade, or having shade equivalence to, for example, a Vita A1-D4 ® Classical Shade or a Vita bleached shade (when tested according to the Shade Matching test provided herein). Shaded ceramic bodies may be prepared by mixing coloring agents (provided above) with a ceramic material prior to formation as a green body. For example, yttria-stabilized zirconia ceramic powder may be shaded by the addition of coloring agents directly to ceramic powder, or by the addition of coloring agents to zirconia ceramic slurry prior to, or during, a wet processing method. Alternatively, coloring agents may be incorporated into a porous bisque ceramic structure prior to sintering, for example, by processes such as infiltration, painting, dripping, dipping, and the like. Further, sintered bodies may be colorized by methods such as, painting, dipping and the like. Examples of methods for shading zirconia ceramic materials or bodies include, but are not limited to, methods described in commonly owned U.S. Pat. No. 9,095,403, issued Aug. 4, 2015, U.S. Pat. No. 9,505,662, issued Nov. 29, 2016, U.S. Pat. No. 9,512,317, issued Dec. 6, 2016, and US Pub. No. 2018/0237345 A1 published Aug. 23, 2018, each of which are hereby incorporated herein by reference in their entireties.

In some embodiments, shaded yttria-stabilized zirconia ceramic powders or bisque bodies, each having a shade equivalence, for example, to a target Vita A1-D4® Classical shade, or bleached shade, have a percent transmittance at 700 nm (measured on a 1 mm thick sintered ceramic body prepared and measured according to the methods herein) that is less than or equal to 5% lower than the percent transmittance of an equivalent unshaded zirconia ceramic material. For example, the transmittance of a shaded zirconia ceramic material may be less than or equal to 3% lower, or less than or equal to 2% lower, or less than or equal to 0.5% lower, than the percent transmittance of an equivalent yttria-stabilized material in which coloring agents have not been incorporated (when measured on a 1 mm thick fully sintered zirconia ceramic body at 700 nm).

In one embodiment, a sintered yttria-stabilized zirconia ceramic material body comprising between 5.2 mol % and 7.2 mol % yttria and at least one metal-containing coloring agent comprising at least one of Fe, Co, Cu, Pr, Tb, Cr, Ni or Er, having a transmittance greater than 60% at 700 nm (when measured on a 1 mm thick ceramic body sintered to at least 98% of theoretical density), matches a shade from a Vita® Classical A1-D4 (16 shade) Shade Guide or Vita® Classical Shade Guide Shade Guide with Bleached Shades shade guide when tested according to the shade matching evaluation method provided herein. In other embodiments, shaded ceramic bodies made by the methods provided herein, having a shade match to a Vita® Classical A1-D4 (16 shade) Shade Guide or Vita® Classical Shade Guide Shade Guide with Bleached Shades shade guide, have a transmittance greater than 62%, greater than 64%, greater than 65%, greater than 66%, greater than 68%, or between 60 and 71%, or between 63 and 71%, at 700 nm (when measured on a 1 mm thick sintered ceramic body).

In other embodiments, shaded or unshaded yttria-stabilized zirconia ceramic material bodies comprising between 5.2 mol % and 7.1 mol % yttria, have a crystal phase composition comprising less than or equal to 1% monoclinic phase when measured by XRD on a bisqued body. In some embodiments, yttria-stabilized zirconia ceramic material bodies comprising between 5.2 mol % and 6.3 mol % yttria, have less than or equal to 1% monoclinic phase when measured on a bisqued body having a hardness of less than or equal to 0.9 GPa. The sintered ceramic material body may have a flexural strength of greater than or equal to 500 MPa. Optionally, the ceramic bodies comprise an average grain size greater than or equal to 1 µm, such as between 1 µm and 20 µm, or greater than or equal to 2 µm, or greater than or equal to 3 µm, or greater than or equal to 4 µm, or greater than or equal to 8 µm, or between 8 µm and 15 µm, or between 8 µm and 12 µm, when measured on a ceramic body sintered to at least 98% theoretical density of the zirconia ceramic material. In one embodiment, a shaded or unshaded yttria-stabilized zirconia ceramic material comprising between 5.2 mol % and 7.1 mol % yttria, having less than or equal to 1% monoclinic phase when measured on a bisqued body, an average grain size greater than or equal to 8 um when measured on a ceramic body sintered to at least 98% theoretical density of the zirconia ceramic material, has a transmittance of greater than 62% at 700 nm (when measured on a 1 mm thick ceramic body sintered to full density).

In other embodiments, shaded or unshaded yttria-stabilized zirconia ceramic material bodies comprising between 5.5 mol % and 6.5 mol % yttria, less than or equal to 1% monoclinic phase when measured on a bisqued body, and an average grain size greater than or equal to 1 um when measured on a ceramic body sintered to at least 98% theoretical density of the zirconia ceramic material, have a transmittance greater than or equal to 58%, or greater than or equal to 60%, or greater than or equal to 62%, at 700 nm, (when measured on a 1 mm thick ceramic body sintered to full theoretical density). The sintered ceramic material body may have a flexural strength of greater than or equal to 500 MPa.

In other embodiments, shaded or unshaded yttria-stabilized zirconia ceramic material bodies comprising between 5.8 mol % and 6.3 mol % yttria, less than or equal to 1% monoclinic phase when measured on a bisqued body, and an average grain size greater than or equal to 1 um when measured on a ceramic body sintered to at least 98% theoretical density of the zirconia ceramic material, have a transmittance greater than or equal to 58%, or greater than or equal to 60%, or greater than or equal to 62%, at 700 nm (when measured on a 1 mm thick ceramic body sintered to full theoretical density). The sintered ceramic material body may have a flexural strength of greater than or equal to 500 MPa.

Test Methods

Density

For the examples described herein, density calculations of ceramic bodies were determined as follows. The density of green body blocks were calculated by measuring the weight and dividing by the volume calculated from the dimensions of the green block. The density of bisqued body blocks were determined by liquid displacement methods of Archimedes principle. Flat wafers were sectioned or milled from a bisqued block and dried prior to measuring the dry mass. Samples were then saturated with deionized water under vacuum (29-30 in Hg vacuum pressure) for one hour prior to measuring the suspended and saturated masses. All masses were measured to four decimal points precision. Relative densities of the samples were calculated based on theoretical densities corresponding to yttria content as indicated in Table 1.

TABLE 1

Theoretical Densities Of Yttria-Stabilized Zirconia Composition.

| Yttria (mol %) | Density (g/cm$^3$) |
| --- | --- |
| 5.2 | 6.058 |
| 5.3 | 6.056 |
| 5.4 | 6.054 |
| 5.5 | 6.052 |
| 5.6 | 6.050 |
| 5.7 | 6.048 |
| 5.8 | 6.046 |
| 5.9 | 6.045 |
| 6.0 | 6.043 |
| 6.1 | 6.042 |
| 6.3 | 6.037 |
| 6.4 | 6.035 |
| 6.5 | 6.033 |
| 6.7 | 6.030 |
| 6.8 | 6.028 |
| 6.9 | 6.026 |
| 7.0 | 6.025 |
| 7.1 | 6.023 |
| 7.4 | 6.019 |
| 7.9 | 6.011 |
| 8.4 | 5.958 |
| 9.7 | 5.923 |

For purposes herein, a ceramic material that is fully sintered has a density that is about 98%, or greater, of the theoretical density.

Flexural Strength

Samples for three-point bend strength (flexural strength) testing were milled and prepared according to ISO 6872: 2015 for the preparation of strength testing for dental ceramic materials. Results are provided in MPa. Flexural strength bars of ceramic materials were milled out of a bisqued block then ground flat with 1200 grit and 2000 grit SiC polishing paper until visually free of defects. The bisqued bars were ground to a thickness corresponding to approximately 1.68×25×4 mm$^3$ after sintering. After sintering, the central region of both the tensile and compressive surfaces were visually inspected for defects by optical microscope. The side with the fewest observed defects was chosen as the side broken in tension (face-down in the test fixture). Flexural testing was performed on a Shimadzu EZ-Test universal testing machine with a custom built three-point bend fixture according to ISO 6872. The bars were aligned on the two rollers using a metal guide. Sample sets contained at least 5 bars. Flexural strengths were calculated via the measured breaking load and measured dimensions.

Fracture Toughness Test

Samples for fracture toughness testing were milled and sintered. Tabs of ceramic materials were milled out of a bisqued block. The bisqued tabs have the dimensions of approximately Φ=13-15 mm, thickness=1-5 mm after sintering. Polishing was carried out to obtain a scratch-free surface according to the polishing steps of Table 2.

TABLE 2

Polishing Steps For Fracture Toughness Sample Preparation.

| Polishing media | Force (lbs) | Head speed | Plate Speed | During time |
| --- | --- | --- | --- | --- |
| 30 μm disc | 30 | 150 | 300 | 2 min |
| 1200 μm disc | 30 | 150 | 300 | 5 min |
| 15 μm diamond polishing solution | 30 | 150 | 300 | 5 min |
| 3 μm diamond polishing solution | 30 | 120 | 120 | 4 min |
| 1 μm diamond polishing solution | 30 | 120 | 120 | 3 min |
| 0.06 μm SiO$_2$ polishing solution | 30 | 120 | 120 | 2 min |

The polished side with the fewest observed defects was chosen as the side for fracture toughness test. Fracture toughness testing was performed on a Shimadzu Micro Hardness Tester (HMV-G21) testing machine with a Vickers indenter fixture. The length of the crack and indentation diagonal were measured by built-in optical microscope (×10, ×40). The method of testing fracture toughness was based on Brian Lawn's calculation (1980) and G. R. Anstis (J. Am. Ceram. Soc., 64(9), P533-538, 1981), using the equation:

$$K_{IC} = 0.0205 * \sqrt[2]{\frac{E}{H}} * \frac{P}{\sqrt[3/2]{C}}$$

wherein $K_{ic}$: Fracture Toughness (MPa·m$^{-1/2}$); E: Young's modulus (GPa); H: Vickers hardness (GPa)*, calculated by $$H = 1.854 * \frac{P}{d^2}$$

wherein P: applied load (N); C: crack length from the center of the impression to the crack tip; d: the length of the indentation diagonal. (Hardness Measurement Ref.: Vander, G. F. (2000). Microindentation hardness testing according to H. Kuhn & D. Medlin (Eds.), ASM Handbook, Volume 8: Mechanical Testing and Evaluation (pp. 221-231). ASM International.)

Translucency

Sintered body translucency was determined by measuring the percent transmittance of D65 light at a wavelength of 700 nm from a 1 to 1.1 mm thick sintered sample. Translucency wafers were sectioned or milled from a bisqued block and machined to a diameter corresponding to a final diameter of approximately 30 mm after sinter. The wafers were then ground flat until visually free of defects with 1200 grit and 2000 grit SiC polishing paper. The final bisqued thickness corresponded to 1 mm after sintering and polishing. Samples ground to the desired shape were removed of surface dust and then sintered according to the sintering profile(s) described herein.

After sintering, the samples were polished prior to testing. A polishing procedure was performed using three separate polishing diamond suspensions to remove scratches, 15 μm, 3 μm, and 1 μm, at a rotating speed of 300 rpm for a dwell time of about 5 to 15 minutes, using hand pressure (approximately 2 to 3 pounds).

Total transmittance spectra were measured between the wavelengths of 360 nm to 740 nm with a Konica-Minolta CM5 spectrophotometer illuminated by a D65 light source for all samples. Information contained in the data tables herein refer to measurements at 700 nm or 500 nm wavelengths, as indicated, which are extracted from these measurements. The spectrophotometer was calibrated to white and black prior to measurement. Translucency samples were placed flush against the (approximately) 25 mm integrating sphere aperture. A minimum of two spectra were collected per sample and averaged to yield a final measured transmittance spectra (S-TM). Collected transmittance data may be reported as "percent (%) transmittance".

Opacity Measurement

Wafers with a thickness of 1±0.1 mm, polished according to the Translucency Test Method, were measured between the wavelength of 400 nm to 700 nm with a Konica-Minolta CM5 spectrophotometer at opacity mode (reflection mode; Specular Component type: SCI; Measurement area diameter=8 mm) illuminated by a D65 light source for all samples. Before testing, the machine was calibrated. The wafers were measured under the white and dark background. A white calibration tile (Avian Technologies LLC, FWT-99-02C) was used for the white background. The dark background using a zero calibration box (Konica Minolta, CM-A124). A minimum of two spectra were collected per sample and averaged to yield the final measured opacity.

Color Space (CIE L*a*b*) Test

Zirconia materials measured for color space were analyzed according to CIE L*a*b* (International Commission on Illumination, measuring two polar axes for color, 'a*' and 'b*', and value (lightness, L*)) values using a Konica Minolta Spectrometer with a D65 light source.

Sintered test wafers having 27 mm diameter were cut or milled from bisque blocks. The final thickness of the test wafers after sintering was 1 mm. Therefore, the starting thickness for each wafer was calculated based on the targeted final thickness taking into consideration the enlargement factor (EF) as follows:

Final thickness×(EF)=bisque wafer thickness.

To measure color, the Konica Minolta CM5 Spectrometer was set on reflectance mode using the Specular Component Excluded (SCE) mode, with a D65 light source, and 11 mm target mask (aperture diameter). The L*a*b* values were measured with the samples placed flush and centered against the aperture with no backing material to back-reflect light. These values were referenced to materials made from traditional processes.

Shade Matching Evaluation

Shade evaluation and shade matching was performed by visual method using a full-spectrum balanced light source, the CIE Standard Illuminant D50 with a correlated color temperature (CCT) of 5000 K. Shaded, fully sintered zirconia ceramic bodies prepared by methods disclosed herein were visually evaluated by the unaided eye under the light source to confirm shade matching to a target shade of the Vita Classical A1-D4® Shade Guide (containing shades B1, A1, B2, D2, A2, C1, C2, D4, A3, D3, B3, A3.5, B4, C3, A4, C4, as arranged by brightness (value), and Vita Bleached Shades.

X-Ray Diffraction (XRD)

The crystal phase of bisque state zirconia ceramic bodies were measured by X-Ray diffractometer (XRD, Rigaku SmartLab, Japan), using CuKα radiation. The measurement conditions were as follows:

radiation source: CuKα (λ=1.541862 Å); measurement mode: step scanning; scanning condition: 1° per minute; step width: 0.02 deg; scattering slit: 5.0 deg; scattering slit: 5.0 deg; receiving slit #1: 4.0 deg; receiving slit #2: 13.0 mm; scanning mode: continuous mode; and scanning range (2θ): 20°-80°.

By analyzing an XRD pattern, tetragonal (t)-cubic (c) phase ratio was calculated by Equation (1)

$$(t+c)\text{phase ratio }(\%)=100-f_m \quad (1)$$

where, $f_m$ is the crystal ratio (%) of monoclinic phase (m), obtained by Equation (2)

$$f_m(\%) = \frac{I_m(111) + I_m(11\bar{1})}{I_m(111) + I_m(11\bar{1}) + I_c(111) + I_t(101)} \times 100 \quad (2)$$

where, $I_m(111)$ is the XRD peak intensity of the monoclinic phase (111) plane; $I_m(11\bar{1})$ is the XRD peak intensity of the monoclinic phase (11$\bar{1}$) plane; $I_t(101)$ is the XRD peak intensity of the tetragonal phase (101) plane; and $I_c(111)$ is the XRD peak intensity of the cubic phase (111) plane, and, where XRD peak intensities were measured with background removed.

Mercury Porosimetry

Pore size and pore size distributions were measured on a 1 gram to 4 gram sample obtained from a bisqued block. Samples were dried before mercury intrusion. Intrusion was performed with a Micromeritics Autopore V porosimeter with set pressure ranges from total vacuum to 60,000 psi using Micromeritics penetrometers models #07 and #09. The median pore diameter (volume) from the measurement was reported as the Median pore diameter.

Particle Size Distribution

Particle size distributions were measured with a Brookhaven Instruments Corp. X-ray disk centrifuge analyzer. Samples were collected from the source suspension and kept agitated until measurement.

Grain Size Measurement

Grain size measurements were performed on sintered materials as outlined in ASTM E112-10, Standard Test Method for Determining Average Grain Size. Sintered samples were polished to remove surface roughness, and thermally etched for 10-30 minutes in an oven heated to 1400° C., and a gold coating was applied to the etched samples. The samples were analyzed by FEI Magellan™ 400 Scanning Electron Microscope. The average grain size was estimated according to the Heyn (4) Lineal Intercept Procedure by counting the number of grains intercepted by one or more straight lines sufficiently long to yield at least 50 intercepts. The magnification of the samples was as follows: for average grain size less than 0.5 μm, ×25000 magnification; grain size from 0.5 μm to 1.5 μm, ×12000 magnification; grain size larger than 1.5 μm, ×5000 or ×12000, magnification; grain size larger than 3 μm, ×2500 magnification; grain size larger than 5 μm, ×1500 magnification; and for grain size larger than 10 μm, ×800 magnification.

Example 1 Through Example 44

Green Body and Bisqued Body Manufacturing Using Wet Processing and Slip-Casting

Zirconia ceramic green bodies and zirconia ceramic bisqued bodies were prepared using a slurry manufacturing and slip-casting method.

Zirconia ceramic materials were selected having a range of yttria content. Commercial name or nominal value as per the manufacturer (Tosoh USA), as well as the actual mol % yttria, is indicated for each zirconia ceramic material A through F, as indicated in Table 3. For example, yttria-stabilized zirconia ceramic material C, nominally referred to as "TZ-3Y", comprised 2.9 mol % yttria according to product sheets provided by the manufacturer for the lot used, and the yttria-stabilized zirconia ceramic material D, nominally referred to as "TZ-PX430" which may be commercially known as "5.5Y", comprised yttria-stabilized zirconia ceramic material stabilized by 5.3 mol ° % yttria. Approximate mean particle sizes of zirconia ceramic agglomerates, prior to wet processing steps described herein, are between 0.2 µm to 2 µm.

TABLE 3

Amount Yttria (Mol %) Of Zirconia Ceramic Materials.

| | Zirconia Ceramic Material Compositions | | | | | |
|---|---|---|---|---|---|---|
| | A | B | C | D | E | F |
| Nominal/ Commercial name | TZ-0Y | PX245 | TZ-3YS | TZ-PX430 | TZ-8YS | TZ-10YS |
| mol % yttria | 0 | 3.0 | 2.9 | 5.3 | 7.9 | 9.7 |

Ceramic slurries were prepared that comprised blends of unstabilized zirconia ("A") and/or yttria-stabilized zirconia ceramic materials ("B" through "F") of Table 3, as indicated in Table 4. Weight ratios of the unstabilized zirconia and/or yttria-stabilized zirconia ceramic materials blended to prepare each Example is provided. The resulting amounts of yttria for each example was calculated and provided in Table 4, reported as yttria mol %.

TABLE 4

Yttria-Stabilized Zirconia Compositions, Particle Size Distributions, And Pore Size Of Bisque Bodies.

| | | Zirconia Ceramic Powders (wt %) | | | | | | Particle size distribution (nm) | | | pore size |
|---|---|---|---|---|---|---|---|---|---|---|---|
| | Yttria | A 0 mol % yttria | B 3 mol % yttria | C 2.9 mol % yttria | D 5.3 mol % yttria | E 7.9 mol % yttria | F 9.7 mol % yttria | D10 | D50 | D90 | |
| Ex. # | Mol % | | | | | | | | | | (nm) |
| 1 | 5.2 | — | — | 0.10 | 0.86 | — | 0.04 | 186 | 253 | 342 | 56 |
| 2 | 5.2 | — | 0.04 | — | 0.96 | — | — | 160 | 237 | 336 | 52 |
| 3[1] | 5.2 | — | 0.04 | — | 0.96 | — | — | 139 | 204 | 329 | 44 |
| 4 | 5.3 | — | 0.53 | — | — | 0.47 | — | 149 | 255 | 348 | 45 |
| 5 | 5.3 | — | — | — | 1.00 | — | — | 168 | 236 | 332 | 48 |
| 6 | 5.4 | — | — | 0.50 | — | 0.50 | — | 234 | 287 | 372 | 70 |
| 7 | 5.4 | — | 0.50 | — | — | 0.50 | — | 137 | 246 | 349 | 48 |
| 8 | 5.4 | — | — | — | 0.98 | — | 0.02 | 162 | 240 | 346 | 54 |
| 9 | 5.5 | — | — | 0.48 | — | 0.52 | — | 229 | 286 | 373 | 74 |
| 10 | 5.5 | — | — | — | 0.92 | 0.08 | — | 173 | 253 | 345 | 55 |
| 11 | 5.5 | — | 0.49 | — | — | 0.51 | — | 150 | 233 | 306 | 44 |
| 12 | 5.6 | — | — | — | 0.88 | 0.12 | — | 176 | 254 | 348 | 59 |
| 13 | 5.7 | — | — | — | 0.84 | 0.16 | — | 179 | 257 | 349 | 56 |
| 14 | 5.8 | — | — | — | 0.89 | — | 0.11 | 215 | 296 | 392 | 75 |
| 15 | 5.8 | — | — | — | 0.80 | 0.20 | — | 174 | 257 | 345 | 57 |
| 16 | 5.8 | — | — | 0.05 | 0.70 | 0.25 | — | 184 | 270 | 381 | 54 |
| 17 | 5.8 | — | 0.42 | — | — | 0.58 | — | 142 | 237 | 324 | 44 |
| 18 | 5.8 | — | 0.38 | — | 0.10 | 0.52 | — | 155 | 245 | 342 | 45 |
| 19 | 5.9 | — | — | — | 0.76 | 0.24 | — | 181 | 263 | 378 | 59 |
| 20 | 5.9 | — | — | 0.20 | 0.40 | 0.40 | — | 206 | 282 | 365 | 66 |
| 21 | 5.9 | — | 0.57 | — | — | — | 0.43 | 131 | 242 | 335 | 46 |
| 22 | 5.9 | — | — | 0.40 | — | 0.60 | — | 237 | 293 | 368 | 75 |
| 23 | 5.9 | 0.2 | — | — | 0.16 | 0.64 | — | 181 | 256 | 342 | 57 |
| 24[2] | 5.9 | 0.2 | — | — | 0.16 | 0.64 | — | 205 | 288 | 361 | 60 |
| 25 | 5.9 | 0.25 | — | — | — | 0.75 | — | 171 | 254 | 346 | 54 |
| 26 | 6.0 | — | — | — | 0.73 | 0.27 | — | 174 | 254 | 361 | 58 |
| 27 | 6.1 | — | — | — | 0.68 | 0.32 | — | 191 | 266 | 362 | 63 |
| 28 | 6.1 | — | — | — | 0.82 | — | 0.18 | 169 | 249 | 348 | — |
| 29 | 6.3 | — | — | — | 0.60 | 0.40 | — | 186 | 265 | 355 | 60 |
| 30 | 6.4 | — | — | — | 0.56 | 0.44 | — | 177 | 251 | 342 | 57 |
| 31 | 6.5 | — | — | — | 0.52 | 0.48 | — | 194 | 265 | 370 | 57 |
| 32 | 6.7 | — | — | — | 0.48 | 0.52 | — | 187 | 256 | 360 | 58 |
| 33 | 6.8 | — | — | — | 0.44 | 0.56 | — | 205 | 269 | 364 | 57 |
| 34 | 6.9 | — | — | — | 0.65 | — | 0.36 | 199 | 271 | 347 | 55 |
| 35 | 6.9 | — | — | — | 0.40 | 0.60 | — | 194 | 266 | 351 | 60 |
| 36 | 7.0 | — | 0.40 | — | — | — | 0.60 | 162 | 253 | 338 | 48 |
| 37 | 7.0 | — | 0.18 | — | — | 0.82 | — | 201 | 268 | 343 | 55 |
| 38 | 7.0 | — | 0.18 | — | — | 0.82 | — | 155 | 220 | 288 | 48 |

TABLE 4-continued

Yttria-Stabilized Zirconia Compositions, Particle Size Distributions, And Pore Size Of Bisque Bodies.

| | | Zirconia Ceramic Powders (wt %) | | | | | | Particle size distribution (nm) | | | pore size (nm) |
|---|---|---|---|---|---|---|---|---|---|---|---|
| Ex. # | Yttria Mol % | A 0 mol % yttria | B 3 mol % yttria | C 2.9 mol % yttria | D 5.3 mol % yttria | E 7.9 mol % yttria | F 9.7 mol % yttria | D10 | D50 | D90 | |
| 39 | 7.0 | — | 0.18 | — | — | 0.82 | — | 170 | 228 | 299 | 46 |
| 40 | 6.96 | — | — | — | 0.36 | 0.64 | — | 204 | 269 | 354 | 60 |
| 41 | 7.1 | — | — | — | 0.32 | 0.68 | — | 215 | 272 | 361 | 60 |
| 42 | 7.4 | — | — | — | 0.20 | 0.80 | — | 223 | 278 | 359 | 63 |
| 43 | 7.9 | — | — | — | — | 1.00 | — | 240 | 296 | 381 | 74 |

[1]flow rate of 2 kg/hour;
[2]flow rate of 8 kg/hour

Zirconia ceramic materials of Table 4, and 0.004 g/g $ZrO_2$ to 0.006 g/$ZrO_2$ dispersant (Dolapix CE 64), were added to deionized water to form a slurry having about 70 wt % to 80 wt % solids concentration (solid loading) to create zirconia ceramic material mixtures having the indicated amount of yttria (mol % yttria). The slurries were mixed using a horizontal bead milling process with zirconia-based media (0.4 mm diameter) at a flow rate of approximately 6 kg/hour (except where otherwise noted) and a mill speed of 2000 rpm to obtain the ceramic slurry for slip-casting. Viscosities for examples ranged from 4 Pa·s to 11 Pa·s, at 80 cpm and 200 cpm.

After milling, the slurries were drained from the horizontal bead mill and passed through a 20 μm sieve to remove milling media and other contamination. Particle size distribution of the resulting slurries were measured according to the methods described herein and reported in Table 4.

Ceramic slurries obtained for each example of Table 4 were vacuum cast into molds to form cast blocks. Molds were used to form disk shaped blocks having a first size of 98 mm diameter×15 mm thickness. After casting, the blocks were placed in a dryer at ambient temperature and weighed at 12 hour increments until the weight of the block had stabilized. Dry green body blocks were loaded into a bisquing oven where the blocks were bisque fired at a final hold temperature of 950° C. for a hold time of 2 hours to form bisqued body blocks.

Median pore sizes were calculated for bisque bodies according to the methods described herein and reported in Table 4. Relative densities of bisqued bodies prepared according to the slip-casting and bisquing methods described herein were in the range of 53% to 63% of theoretical densities when measured according to Density Test Method according to Archimede's principle, as provided herein.

Sintered Yttria-Stabilized Zirconia Ceramic Bodies

Zirconia sintered bodies were prepared from bisqued blocks described above. Zirconia wafers were milled from the prepared bisqued blocks and were sintered substantially according to the sintering profile of FIG. 4 (except where indicated).

Translucencies of sintered bodies prepared and measured by the methods described herein as total light transmittance, were reported as percent transmittance values obtained at 700 nm (T %@700 nm) and 500 nm (T %@500 nm), reported in Table 5. Translucencies of some sintered bodies are graphically represented in FIG. 6, for the range of 350 nm through 700 nm.

Density, flexural strength, fracture toughness (by optical microscope), grain size and opacity, tested and measured according to the methods described herein, are provided in Table 5, and the total amount of yttria in the samples measured is listed as $Y_2O_3$ mol %.

TABLE 5

Properties Of Sintered Yttria-Stabilized Zirconia Ceramic Bodies.

| Ex. # | Yttria Mol % | T % @ 700 nm | T % @ 500 nm | Flexural Strength (MPa) | Relative Density (%) | Opacity | Grain Size (μm) | Fracture Toughness (MPa · m$^{1/2}$) |
|---|---|---|---|---|---|---|---|---|
| 1 | 5.2 | 58.5 | 49.3 | 785 | 60 | 53.6 | 1.3 | — |
| 2 | 5.2 | 58.8 | 49.6 | 792 | 60 | 59.1 | 1.2 | — |
| 3 | 5.2 | 59.2 | 49.9 | 738 | 60 | 59.1 | — | — |
| 4 | 5.3 | 59.3 | 49.2 | — | 61 | 59.4 | 1.5 | 2.6 |
| 5 | 5.3 | 59.9 | 50.7 | 746 | 59 | 58.8 | 1.4 | — |
| 6 | 5.4 | 58.8 | 48.7 | 726 | 58 | 59.9 | — | — |
| 7 | 5.4 | 62.0 | 50.3 | 635 | 61 | 57.0 | 1.8 | 2.7 |
| 8 | 5.4 | 60.8 | 50.5 | 695 | 60 | 57.6 | — | — |
| 9 | 5.5 | 61.2 | 49.8 | 630 | 59 | 57.9 | — | — |
| 10 | 5.5 | 64.0 | 52.5 | 680 | 61 | 54.9 | 1.9 | — |
| 11 | 5.5 | 63.5 | 51.5 | | 61 | 55.4 | — | — |
| 12 | 5.6 | 65.4 | 56.7 | 732 | 60 | 51.3 | 2.1 | — |
| 13 | 5.7 | 68.1 | 56.2 | 652 | 60 | 46.5 | 2.5 | 2.1 |
| 14 | 5.8 | 68.9 | 56.7 | 597 | 60 | 48.7 | 3.2 | — |
| 15 | 5.8 | 69.2 | 57.3 | 645 | 60 | 48.1 | — | 2.2 |

TABLE 5-continued

Properties Of Sintered Yttria-Stabilized Zirconia Ceramic Bodies.

| Ex. # | Yttria Mol % | T % @ 700 nm | T % @ 500 nm | Flexural Strength (MPa) | Relative Density (%) | Opacity | Grain Size (μm) | Fracture Toughness (MPa·m$^{1/2}$) |
|---|---|---|---|---|---|---|---|---|
| 16 | 5.8 | 67.8 | 56.1 | 635 | 61 | 49.7 | 3.3 | 2.3 |
| 17 | 5.8 | 68.6 | 56.0 | — | 62 | 48.9 | 3.6 | — |
| 18 | 5.8 | 68.5 | 55.9 | — | 61 | 49.3 | — | — |
| 19 | 5.9 | 68.8 | 58.2 | 603 | 60 | 46.3 | 3.6 | 2.3 |
| 20 | 5.9 | 67.2 | 55.1 | 540 | 59 | 51.2 | 3.3 | — |
| 21 | 5.9 | 67.5 | 53.7 | 551 | 61 | 52.1 | 3.3 | 2.3 |
| 22 | 5.9 | 67.3 | 54.6 | 560 | 58 | 51.5 | 3.0 | 2.3 |
| 23 | 5.9 | 66.2 | 53.8 | 613 | 60 | 52.1 | — | — |
| 24 | 5.9 | 64.8 | 52.8 | — | 59 | 54.0 | 3.4 | — |
| 25 | 5.9 | 67.8 | 54.8 | — | 61 | 50.9 | 3.7 | 2.3 |
| 26 | 6.0 | 69.3 | 59.1 | 631 | 60 | 46.2 | 3.8 | 2.3 |
| 27 | 6.1 | 70.0 | 59.6 | 603 | 60 | 46.3 | 4.9 | — |
| 28 | 6.1 | 70.4 | 59.6 | — | 61 | 46.0 | — | — |
| 29 | 6.3 | 69.0 | 60.4 | 533 | 60 | 45.7 | 4.2 | 2.1 |
| 30 | 6.4 | 66.5 | 57.7 | 580 | 60 | 47.7 | 4.0 | 2.1 |
| 31 | 6.5 | 66.1 | 57.3 | 575 | 60 | 46.6 | 4.1 | — |
| 32 | 6.7 | 65.0 | 56.0 | 543 | 60 | 49.3 | 4.2 | 2.1 |
| 33 | 6.8 | 62.0 | 53.1 | 571 | 60 | 53.1 | 4.0 | 2.1 |
| 34 | 6.9 | 59.1 | 50.6 | 494 | 61 | 58.0 | — | — |
| 35 | 6.9 | 65.0 | 56.0 | 552 | 61 | 44.7 | 4.8 | 1.8 |
| 36 | 7.0 | 64.3 | 55.7 | 453 | 62 | 49.6 | — | — |
| 37 | 7.0 | 64.5 | 56.2 | 499 | 62 | 46.7 | 4.0 | 1.9 |
| 38 | 7.0 | 63.4 | 54.8 | — | 63 | 48.8 | — | — |
| 39 | 7.0 | 63.8 | 55.6 | — | 63 | 47.3 | — | — |
| 40 | 7.0 | 59.1 | 50.2 | 465 | 60 | 57 | — | — |
| 41 | 7.1 | 58.9 | 50.0 | 425 | 60 | 56.8 | 4.4 | 1.9 |
| 42 | 7.4 | 55.6 | 47.2 | — | 60 | 61.1 | 5.0 | 1.8 |
| 43 | 7.9 | 54.0 | 45.5 | — | 58 | 62.0 | 4.7 | — |

[1] flow rate of 2 kg/hour;
[2] flow rate of 8 kg/hour

FIG. 7A is an SEM of sintered body of Example 16, which comprises a blend of three yttria-stabilized zirconia ceramic materials that provide 5.8 mol % yttria in yttria-stabilized zirconia. Upon sintering the material provides an average grain size of 3.3 μm, flexural strength greater than 600 MPa, fracture toughness of 2.3 MPa·m$^{-1/2}$, and percent transmittance of 67.8% at 700 nm (total light transmittance, 1 mm thick sintered body).

To test the effect of flow rate, yttria stabilized zirconia ceramic bisque bodies were prepared as described above, using yttria-stabilized zirconia material compositions described in Table 5. A flow rate of 2 kg/hour, and 8 kg/hour, was measured for Examples 3 and 24, respectively, in addition to the flow rate of 6 kg/hour.

Figure 4:
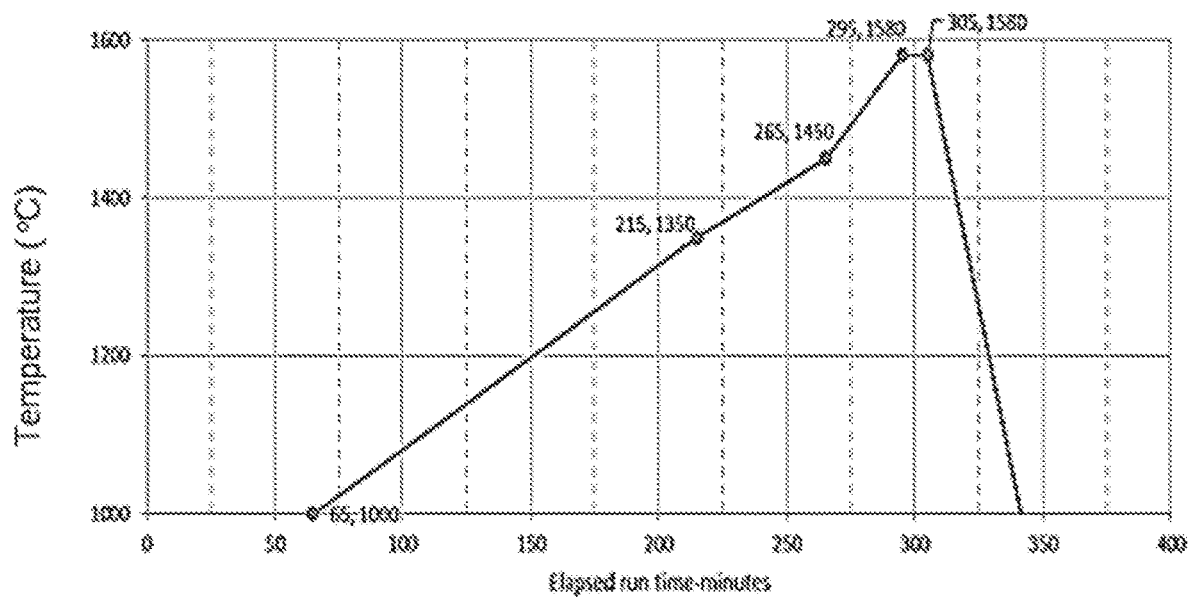
FIG. 4. A graphical representation of one embodiment of a sintering profile suitable for sintering yttria-stabilized zirconia ceramic bodies.

To test the effect of hold time during sintering on translucency, bisque bodies were sintered substantially according to FIG. 4, having a hold time at 1580° C. of 10 minutes for Examples 15, 37 and 44, and by modifying the sintering profile of FIG. 4 to have a hold time at 1580° of 300 minutes, as indicated in Table 6, for Examples 15b, 37b, and 44b. Translucency is measured and reported as percent transmittance at 700 nm in Table 6.

TABLE 6

Sintered Yttria-Stabilized Zirconia Bodies Translucency.

| | | Raw material | | | | Percent Transmittance (@700 nm) | |
|---|---|---|---|---|---|---|---|
| | | B | D | E | F | | |
| | Yttria | (3.0 mol %) | (5.3 mol %) | (7.9 mol %) | (9.7 mol %) | | |
| Ex. # | (mol %) | yttria) | yttria) | yttria) | yttria) | 10 min | 300 min |
| 15/15b | 5.8 | — | 0.8 | 0.2 | — | 69.2 | 73.0 |
| 37/37b | 7.0 | 0.18 | — | 0.82 | — | 64.5 | 67.0 |
| 44/44b | 6.1 | 0.37 | — | — | 0.63 | 71.1 | 73.6 |

XRD analysis was performed on Examples 19, and 21 through 23, each having 5.9 mol % yttria-stabilized zirconia ceramic obtained through blends of different combinations of zirconia ceramic raw materials, to analyze crystal phases. Bisqued bodies were analyzed by XRD according to the method described herein. The results of crystal phase analysis of bisque bodies, and translucencies obtained after sintering the materials of Examples 19, and 21 through 23, (for total light transmittance at 700 nm for 1 mm sintered sample), are provided in Table 7. XRD analysis is graphically represented in FIGS. 5a through 5g, and compared to starting materials A, D and F.

Zirconia materials prepared having a range of yttria content (mol %) comprised blends of zirconia ("A through "F") of Table 3. Zirconia test samples were prepared from bisqued blocks and were sintered according to one of two sintering profiles outlined in Tables 9 and 10. The sintering profile used for each sample is set forth in Table 11.

Figure 3B:
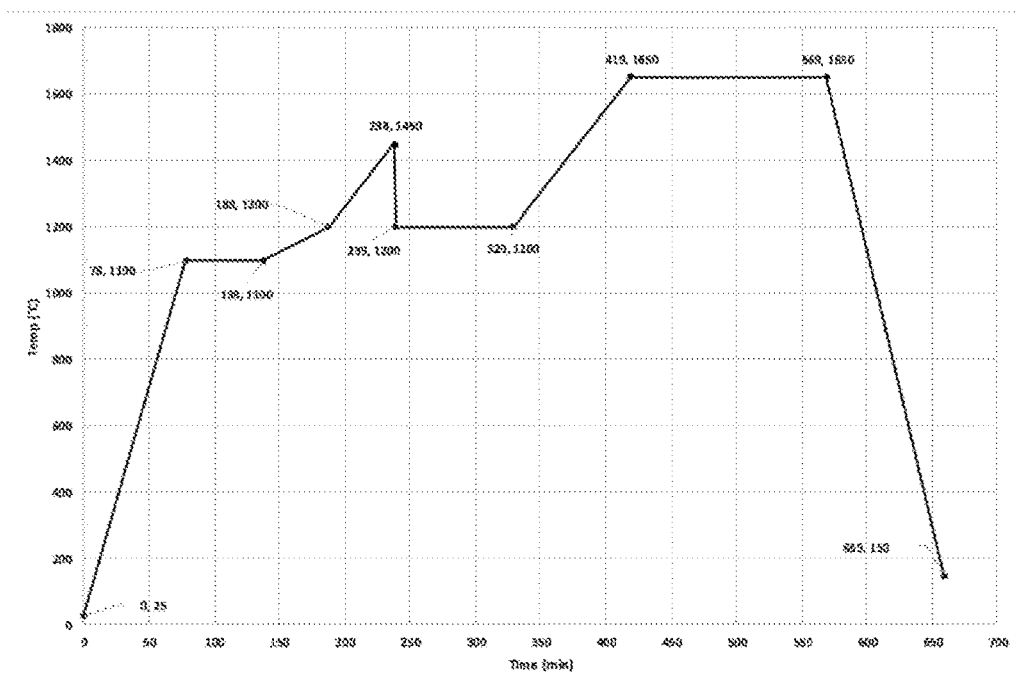

Ceramic bodies sintered according to Table 9, were heated to a maximum oven temperature of 1650° C. having a hold time at that temperature for 150 minutes, substantially according to the sintering profile of Table 9 (denoted 1650 C/150 min) and FIG. 3B.

TABLE 7

XRD And Translucency For Yttria-Stabilized Zirconia Bodies.

| Ex. # | Yttria (mol %) | Powder | Phase Analysis | | | Phase Composition | | T % 700 nm | T % 500 nm |
|---|---|---|---|---|---|---|---|---|---|
| | | | Mono-clinic | Tetra-gonal | Cubic | Mono-clinic % | (t + c) % | | |
| 19 | 5.9 | 0.76 D + 0.24 E | | ✓ | ✓ | 0.0% | 100.0% | 68.8 | 58.2 |
| 21 | 5.9 | 0.57 B + 0.43 F | ✓ | ✓ | ✓ | 7.4% | 92.6% | 67.5 | 53.7 |
| 22 | 5.9 | 0.40 C + 0.60 E | ✓ | ✓ | ✓ | 7.5% | 92.5% | 67.3 | 54.6 |
| 23 | 5.9 | 0.20 A + 0.64 E + 0.16 D | ✓ | ✓ | ✓ | 12.5% | 87.5% | 66.2 | 53.8 |
| A | 0.0 | 100% A | ✓ | | | 100.0% | 0.0% | n/a | |
| D | 5.3 | 100% D | | ✓ | | 0.0% | 100.0% | | |
| G | 9.7 | 100% F | | | ✓ | 0.0% | 100.0% | | |

Shaded samples were prepared comprising the zirconia material according to Example 15. The porous wafers were colored before sintering by painting with coloring solutions targeted to match a B1 and B2 shade of Vita Classical A1 through D4® Shade Guide (Vita North America) upon sintering. The colored wafers were sintered according to the sintering profile of FIG. 4. Wafers were polished and measured according to the Translucency and Color Space test methods (measuring 1 mm thick wafers). The results are provided in Table 8.

TABLE 8

Color Space and Translucency Results Of Colored Yttria-Stabilized Zirconia Sintered Bodies.

| Ex. # | L*(D65) | a*(D65) | b*(D65) | T % @700 nm | T % @500 nm |
|---|---|---|---|---|---|
| 15 | — | — | — | 69.2 | 57.3 |
| 15c-target B1 | 50.1 | -4.7 | -3.6 | 66.7 | 51.8 |
| 15d-target B2 | 49.8 | -5.2 | -1.6 | 66.6 | 51.0 |

Percent transmittance measurements at 700 nm (1 mm fully sintered ceramic body) were approximately 2.5% lower than the uncolored samples.

Example 45 Through Example 62

Ceramic slurries, green bodies and bisque bodies were made substantially according to the wet processing, slip casting and bisque heating techniques described above for Examples 1 through 44.

TABLE 9

Multi-Step Sintering Profile (To 1650° C.) For Zirconia Ceramic Bodies.

| Temp 1 ° C. | Time 1 | Elapsed time | Start Temp ° C. | Heating rate (° C./min) |
|---|---|---|---|---|
| 25 | 78 | 0 | 25 | 13.8 |
| 1100 | 60 | 78 | 1100 | 0 |
| 1100 | 50 | 138 | 1100 | 2 |
| 1200 | 50 | 188 | 1200 | 5 |
| 1450 | 1 | 238 | 1450 | -250 |
| 1200 | 90 | 239 | 1200 | 0 |
| 1200 | 90 | 329 | 1200 | 5 |
| 1650 | 150 | 419 | 1650 | 0 |
| 1650 | 90 | 569 | 1650 | -16.7 |
| 150 | | 659 | 150 | — |

Ceramic bodies optionally sintered according to the sintering profile of Table 10, were heated substantially according to Table 9 and FIG. 3B, except the maximum oven temperature was 1620° C., rather than 1650° C., and the hold time at 1620° C. was 15 minutes (denoted as 1620 C/15 min).

TABLE 10

Multi-Step Sintering Profile (To 1620° C.) For Zirconia Ceramic Bodies.

| Temp 1 ° C. | Time 1 | Elapsed time | Start Temp ° C. | Heating rate (° C./min) |
|---|---|---|---|---|
| 25 | 78 | 0 | 25 | 13.8 |
| 1100 | 60 | 78 | 1100 | 0 |
| 1100 | 50 | 138 | 1100 | 2 |
| 1200 | 50 | 188 | 1200 | 5 |
| 1450 | 1 | 238 | 1450 | -250 |

TABLE 10-continued

Multi-Step Sintering Profile (To 1620° C.) For Zirconia Ceramic Bodies.

| Temp 1 ° C. | Time 1 | Elapsed time | Start Temp ° C. | Heating rate (° C./min) |
|---|---|---|---|---|
| 1200 | 90 | 239 | 1200 | 0 |
| 1200 | 83 | 329 | 1200 | 5.1 |
| 1620 | 15 | 412 | 1620 | 0 |
| 1620 | 90 | 427 | 1620 | −16.3 |
| 150 | | 517 | 150 | — |

Weight ratios of zirconia ceramic powders used to prepare blends of Examples 45 to 62 are provided in Table 11; the resulting amount of yttria for each example was calculated and provided in Table 11, reported as yttria mol %.

TABLE 11

Composition Of Sintered Yttria-Stabilized Zirconia Ceramic Bodies Made From Powder Blends.

| Ex. # | Yttria Mol % | Zirconia Ceramic Powders (wt %) | | | | | Sinter Profile |
| | | B 3 mol % yttria | C 2.9 mol % yttria | D 5.3 mol % yttria | E 7.9 mol % yttria | F 9.7 mol % | |
|---|---|---|---|---|---|---|---|
| 45 | 5.0 | 0.15 | | 0.84 | | 0.1 | 1650 C./150 min |
| 46 | 5.2 | | 0.1 | 0.86 | | 0.04 | 1650 C./150 min |
| 47 | 5.2 | | 0.1 | 0.86 | | 0.04 | 1620 C./15 min |
| 48 | 5.2 | | 0.225 | 0.675 | | 0.1 | 1650 C./150 min |
| 49 | 5.2 | 0.04 | | 0.96 | | | 1650 C./150 min |
| 50 | 5.2 | 0.04 | | 0.96 | | | 1620 C./15 min |
| 51 | 5.4 | | | 0.96 | 0.04 | | 1650 C./150 min |
| 52 | 5.4 | | | 0.96 | 0.004 | | 1620 C./15 min |
| 53 | 5.4 | 0.63 | | | | 0.37 | 1650 C./150 min |
| 54 | 5.4 | | | 0.98 | | 0.02 | 1650 C./150 min |
| 55 | 5.4 | | | 0.98 | | 0.2 | 1620/15 min |
| 56 | 5.6 | 0.47 | | | 0.53 | | 1650 C./150 min |
| 57 | 5.6 | | | 0.88 | 0.12 | | 1650 C./150 min |
| 58 | 5.9 | | | 0.76 | 0.24 | | 1650 C./150 min |
| 59 | 6.3 | | | 0.6 | 0.4 | | 1650 C./150 min |
| 60 | 7.1 | | | 0.32 | 0.68 | | 1650 C./150 min |
| 61 | 7.9 | | | 0.41 | | 0.59 | 1650 C./150 min |
| 62 | 8.4 | | | | 0.75 | 0.25 | 1650 C./150 min |

Sintered bodies made from the materials according to Examples 45 to 62 were polished and prepared for translucency analysis according to the methods described herein for total light transmittance (measured on 1 mm thick fully sintered ceramic bodies). Total transmittance spectra were measured according to the method provided herein between the wavelengths of 360 nm to 740 nm with a Konica-Minolta CM5 spectrophotometer illuminated by a D65 light source for all samples. The results were reported as percent transmittance values obtained at 700 nm (T %@ 700 nm) and 500 nm (T %@500 nm) as seen in Table 12. Flexural strength, fracture toughness (by optical microscope), grain size and hardness, were tested and measured according to the methods described herein, and the results are provided in Table 12.

TABLE 12

Properties Of Sintered Yttria-Stabilized Zirconia Ceramic Bodies Made From Powder Blends.

| Ex. # | Yttria Mol % | % T 500 nm | % T 700 nm | Fracture Toughness $MPa \cdot m^{-1/2}$ | Hardness (GPa) | Grain Size (μm) | Flex Strength (MPa) |
|---|---|---|---|---|---|---|---|
| 46 | 5.2 | 53.7 | 65.9 | — | — | 8.0 | — |
| 47 | 5.2 | 50.5 | 62.0 | 2.6 | 13.4 | 2.2 | — |
| 48 | 5.2 | 49.8 | 61.7 | — | — | 3.2 | — |
| 49 | 5.2 | 51.7 | 63.5 | — | — | 13.0 | 616 ± 74 |
| 50 | 5.2 | 50.3 | 61.3 | 2.5 | 13.7 | 1.9 | 735 ± 48 |
| 51 | 5.4 | 59.4 | 71.6 | 2.5 | — | 13.7 | 625 ± 88 |
| 52 | 5.4 | 49.9 | 61.3 | 2.4 | 13.2 | 4.1 | — |
| 53 | 5.4 | 51.1 | 63.3 | — | — | 4.2 | — |
| 54 | 5.4 | 60.1 | 71.9 | — | — | — | 604 ± 59 |
| 55 | 5.4 | 54.2 | 66.0 | 2.4 | 13.3 | 2.4 | — |
| 56 | 5.6 | 58.2 | 73.1 | — | — | 8.5 | — |
| 57 | 5.6 | 62.3 | 76.7 | — | — | — | — |
| 58 | 5.9 | 63.8 | 72.4 | — | — | — | — |
| 59 | 6.3 | 59.9 | 68.6 | 2.1 | 13.1 | 11.9 | 529 ± 76 |
| 60 | 7.1 | 51.9 | 61.3 | 1.7 | 13.1 | 11.1 | 508 ± 28 |
| 61 | 7.9 | 51.1 | 60.2 | — | — | — | — |
| 62 | 8.4 | 48.3 | 57.7 | — | — | — | — |

Images by SEM analysis for Ex. 59 (6.3 mol % yttria) and Ex. 60 (7.1 mol % yttria) which were sintered according to the sintering profile of Table 9, are reproduced in FIGS. 7B and 7C, respectively. Images by SEM analysis for Ex. 48 (5.2 mol % yttria) and Ex. 52 (5.4 mol % yttria) which were sintered according to the sintering profile of Table 10, are reproduced in FIGS. 7D and 7E, respectively. Yttria-stabilized zirconia ceramic materials having the same total yttria concentration but made of different mixtures of ceramic zirconia ceramic powders (e.g., Table 3, A through F) were measured for phase composition and hardness in the bisque stage, and translucency and flexural strength in the sintered stage. Results are reported in Table 13. Bisque stage ceramic bodies having 5.2 mol % yttria, 5.4 mol % yttria, and 5.6 mol % yttria, were measured by XRD analysis to determine percent monoclinic, tetragonal (t) and cubic (c) phases, according to methods provided herein. The bisqued bodies were readily millable, having hardness values of 0.7 GPa or less. Translucency was measured as percent transmittance of a 1 mm thick fully sintered body (% T) at 700 nm.

TABLE 13

XRD, Translucency And Hardness For Yttria-Stabilized Zirconia Bodies.

| | | Peak Intensity | | | Phase Composition | | | |
|---|---|---|---|---|---|---|---|---|
| Ex. # | mol % yttria | $I_m(11\bar{1})$ | $Im(11\bar{1})$ | $I_t(101)$ + $I_c(111)$ | monoclinic % | (t + c) % | Hardness GPa | % T at 700 nm |
| 46 | 5.2 | 0.38 | 0.36 | 98.15 | 0.7% | 99.3% | 0.52 | 65.9 |
| 48 | 5.2 | 0.46 | 0.52 | 98.05 | 1.0% | 99.0% | 0.55 | 61.7 |
| 51 | 5.4 | 0.23 | 0.16 | 98.07 | 0.4% | 99.6% | 0.36 | 71.6 |
| 53 | 5.4 | 1.17 | 1.48 | 97.73 | 2.6% | 97.4% | n/a | 63.3 |
| 54 | 5.4 | 0.20 | 0.11 | 98.11 | 0.3% | 99.7% | 0.59 | 71.9 |
| 56 | 5.6 | 1.36 | 1.44 | 97.86 | 2.8% | 97.2% | 0.70 | 73.1 |
| 57 | 5.6 | 0.29 | 0.25 | 98.19 | 0.5% | 99.5% | 0.59 | 76.7 |

As reported in Table 13, ceramic bodies made from materials of Ex. 46 and Ex. 48 with 5.2 mol % yttria had different concentrations of monoclinic phase (0.7 and 1.0%, respectively) when measured on bisqued ceramic bodies having a hardness less than or equal to 0.55, Ex. 46 had a higher transmittance at 700 nm in the sintered stage (65.9% vs 61.7%, transmittance respectively). Likewise, 5.4 mol % yttria-stabilized materials of Ex. 51 and Ex. 54, having lower percentages of monoclinic phase (0.4% and 0.3%, respectively) compared to Ex. 53 (2.6% monoclinic phase) measured on bisque stage bodies having a hardness less than 0.6 GPa, had higher transmittance (71.6% and 71.9% at 700 nm) in a sintered body compared to Ex. 53 (63.3% at 700 nm), while maintaining a flexural strength greater than 600 MPa in the sintered body. Ceramic materials of Ex. 56 having a higher percentage of monoclinic phase (2.8%) compared to Ex. 57 (0.5% monoclinic phase) measured on bisque stage bodies having a hardness 0.7 GPa or less, had a lower transmittance (73.1% at 700 nm) measured on a 1 mm thick fully sintered body compared to Ex. 57 (76.7% at 700 nm).

We claim:

1. A sintered ceramic body comprising
a yttria-stabilized zirconia ceramic material, stabilized by 5 mol % to 7.2 mol % yttria, wherein the ceramic material formed as a sintered ceramic body has a flexural strength greater than 500 MPa, and a transmittance greater than 62% at 700 nm (when measured on a 1 mm thick fully sintered ceramic body).

2. The sintered ceramic body of claim 1, wherein the sintered ceramic body comprises between 63 and 77% transmittance.

3. The sintered ceramic body of claim 1, wherein the sintered ceramic body has a fracture toughness greater than 1.5 MPa·m$^{-1/2}$.

4. The sintered ceramic body of claim 1, wherein the sintered ceramic body has an average grain size between 1 and 20 μm.

5. The sintered ceramic body of claim 1, wherein the ceramic material comprises between 5.1 mol % and 7.1 mol % yttria, and wherein the sintered ceramic body comprises between 63% and 77% transmittance at 700 nm.

6. The sintered ceramic body of claim 1, wherein the ceramic material comprises between 5.2 mol % and 7.2 mol % yttria, and wherein the sintered ceramic body comprises between 63 and 72% transmittance at 700 nm.

7. The sintered ceramic body of claim 1, wherein the ceramic material comprises between 5.8 mol % and 6.3 mol % yttria and wherein the sintered ceramic body comprises between 63 and 74% transmittance at 700 nm.

8. The sintered ceramic body of claim 7, wherein the sintered body comprises a fracture toughness of greater than 2 MPa·m$^{-1/2}$.

9. The sintered ceramic body of claim 1, wherein the ceramic material comprises between 5 mol % and 6.4 mol % yttria, and wherein the sintered ceramic body comprises between 63% and 78% transmittance at 700 nm.

10. The sintered ceramic body of claim 1, wherein the ceramic material comprises between 5.1 mol % and 6.4 mol % yttria, and wherein the sintered ceramic body comprises between 68% and 75% transmittance at 700 nm.

11. The sintered ceramic body of claim 1, wherein the ceramic material comprises between 5.1 mol % and 6.4 mol % yttria, and wherein the sintered ceramic body comprises between 64% and 70% transmittance at 700 nm.

12. A sintered ceramic body comprising
a yttria-stabilized zirconia ceramic material stabilized by 5.2 mol % to 7.1 mol % yttria,
wherein the sintered ceramic body has a flexural strength greater than or equal to 500 MPa, and
wherein the sintered ceramic body comprising at least 98% theoretical density has an average grain size greater than or equal to 8 μm.

13. The sintered ceramic body of claim 12, wherein the sintered ceramic body has an average grain size between 8 μm and 20 μm.

14. The sintered ceramic body of claim 12, wherein the sintered ceramic body has an average grain size between 8 μm and 15 μm.

15. The sintered ceramic body of claim 12, wherein the yttria-stabilized zirconia ceramic material is shaded by a coloring agent comprising at least one metal selected from Fe, Co, Cu, Pr, Tb, Cr or Er.

16. The sintered ceramic body of claim 12, wherein the sintered ceramic body comprises greater than 60% transmittance at 700 nm (when measured on a 1 mm thick fully sintered ceramic body).

17. A sintered ceramic body comprising
a shaded yttria-stabilized zirconia ceramic material stabilized by 5.5 mol % to 6.5 mol % yttria, comprising a metal-containing component as a coloring agent, and
wherein the sintered ceramic body comprises at least 98% theoretical density and has an average grain size greater than or equal to 1 μm and a transmittance greater than 58% at 700 nm (when measured on a 1 mm thick sintered body).

18. The sintered ceramic body of claim 17, wherein the ceramic material is stabilized by 5.8 mol % to 6.3 mol % yttria.

19. The sintered ceramic body of claim 17, wherein the transmittance is greater than 60% at 700 nm.

20. The sintered ceramic body of claim 17, wherein the transmittance is greater than 62% at 700 nm.

* * * * *